United States Patent
Xu et al.

(10) Patent No.: US 9,353,146 B2
(45) Date of Patent: May 31, 2016

(54) ACYLATION DERIVATIVES OF PARIDIS SAPONINS I, PREPARATION METHOD THEREFOR AND APPLICATION THEREOF

(71) Applicant: HANGZHOU BENSHENG PHARMACEUTICAL CO., LTD., Zhejiang (CN)

(72) Inventors: Rongzhen Xu, Zhejiang (CN); Frank Rong, Zhejiang (CN); Fuwen Xie, Fujian (CN)

(73) Assignee: HANGZHOU BENSHENG PHARMACEUTICAL CO., LTD, Zhejiang (CN)

( * ) Notice: Subject to any disclaimer, the term of this patent is extended or adjusted under 35 U.S.C. 154(b) by 0 days.

(21) Appl. No.: 14/407,622

(22) PCT Filed: Jun. 13, 2013

(86) PCT No.: PCT/CN2013/077165
§ 371 (c)(1),
(2) Date: Dec. 12, 2014

(87) PCT Pub. No.: WO2013/185613
PCT Pub. Date: Dec. 19, 2013

(65) Prior Publication Data
US 2015/0152133 A1    Jun. 4, 2015

(30) Foreign Application Priority Data

Jun. 13, 2012  (WO) ................ PCT/CN2012/076840

(51) Int. Cl.
*C07J 21/00* (2006.01)
*C07J 71/00* (2006.01)
*A61K 31/7048* (2006.01)

(52) U.S. Cl.
CPC ......... *C07J 71/0005* (2013.01); *A61K 31/7048* (2013.01); *C07J 71/00* (2013.01)

(58) Field of Classification Search
None
See application file for complete search history.

(56) References Cited

FOREIGN PATENT DOCUMENTS

| CN | 1322729 A | 11/2001 |
| CN | 101143148 A | 3/2008 |

OTHER PUBLICATIONS

Kong et al., Acta Biochim Biophys Sin—2010, vol. 42(11), pp. 827-833.*
English Translation of the Written Opinion of the International Search Authority for Application No. PCT/CN2013/077165, dated Sep. 19, 2013 (7 pages).
English Translation of the International Search Report for Application No. PCT/CN2013/077165, dated Sep. 19, 2013 (4 pages).
Wang et al. (2007) Bioorganic and Medicinal Chemistry. 15(7):2528-2532.
Supplementary European Search Report with Written Opinion corresponding to European Patent Application No. 13805106.5, dated Oct. 13, 2015.

* cited by examiner

*Primary Examiner* — Traviss C McIntosh, III
(74) *Attorney, Agent, or Firm* — Lathrop & Gage LLP; Brian C. Trinque; Benjamin D. Heuberger

(57) ABSTRACT

The present invention belongs to the field of natural medicine and pharmaceutical chemistry, and relates to novel Polyphyllin I derivatives of formula (I) that is acylated at the 5'-position of arabinofuranosyl or a pharmaceutically acceptable salt thereof, to a process for the preparation of these compounds, compositions containing such compounds and their use in preparing antineoplastic medicaments.

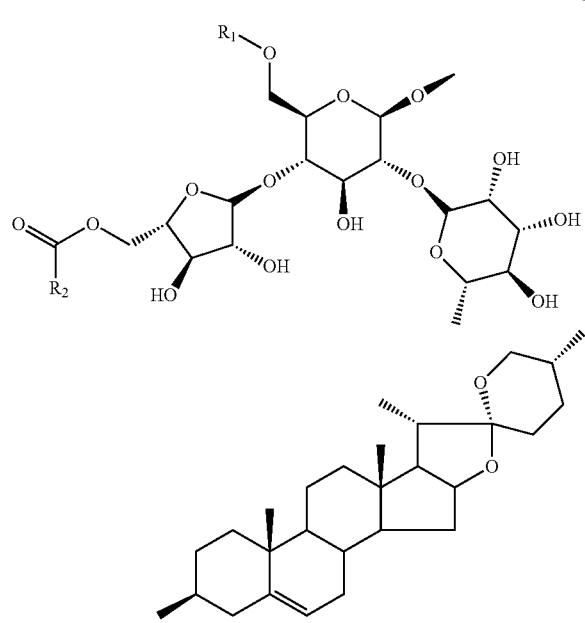

15 Claims, No Drawings

ACYLATION DERIVATIVES OF PARIDIS SAPONINS I, PREPARATION METHOD THEREFOR AND APPLICATION THEREOF

RELATED APPLICATIONS

This application is a 35 U.S.C. §371 filing of International Patent Application No. PCT/CN2013/077165, filed Jun. 13, 2013, which claims priority to International Patent Application No. PCT/CN2012/076840, filed Jun. 13, 2012, each of which is incorporated herein by reference in its entirety.

TECHNICAL FIELD

The present invention belongs to the field of natural medicine and pharmaceutical chemistry, and relates to novel Polyphyllin I derivatives, in particular Polyphyllin I derivatives with 5'-acylated arabinofuranosyl, to a process for the preparation of these compounds, compositions containing such compounds and their use in preparing antineoplastic medicaments.

BACKGROUND OF THE INVENTION

Polyphyllin I, also known as Polyphyllin D and abbreviated as PPD or PPI, is 4-O-arabinofuranosyl-2-O-rhamnopyranosyl-β-D-glucopyranosyldioscin, a small molecular monomer extracted from the traditional Chinese medicine Paris Polyphylla also known as windpipe trachea. Paris Polyphylla has antibacterial, anti-inflammatory, analgesic, tranquilizing, and antitumor effects. Research has found that its main active component, Polyphyllin I, exerts its antitumor effects mainly by means of inducing apoptosis. Polyphyllin I has significant inhibitory effects on various tumor cells and is considered a natural medicine with good application prospect.

Studies have reported that the effects of Polyphyllin I on the radiosensitivity of nasopharyngeal carcinoma CNE-2 cell line are observed by using DDP as a positive control, said DDP having significant sensitizing effects on nasopharyngeal carcinoma. Results have shown that Polyphyllin I has time- and dose-dependent inhibitory effects on the proliferation of CNE-2 cells and has concentration-dependent radiosensitizing effects on the cell lines (HUA Yonghong et al., Effect of Polyphyllin I on Radiosensitivity in Nasopharyngeal Carcinoma Cell Line CNE-2 in vitro, Chinese Archives of Traditional Chinese Medicine, Vol. 29(6), 2011, pp. 1387).

XIAO Meifang et al. have discussed the in vitro effects of Polyphyllin I on the proliferation and apoptosis of human hepatocellular carcinoma SMMC-7721 cell line and related mechanisms. Studies have shown that Polyphyllin I can inhibit the proliferation of hepatocellular carcinoma SMMC-7721 cells in a time- and concentration-dependent manner. It is possible that Polyphyllin I inhibits the proliferation of the hepatocellular carcinoma cells via the mechanism of retarding the growth of the tumor cells and inducing cell apoptosis (XIAO Meifang et al., Growth and Apoptosis Effects of Paris Saponin I on Human Hepatocellular Carcinoma Cells, Life Science Research, Vol. 15(6), 2011, pp. 519).

It is discovered in the studies on Polyphyllin I that very few literatures has reported on modifying the free hydroxyl of Polyphyllin I. YU Biao et al have prepared several acylated dioscin compounds by taking advantage of the catalysis of lipase, which includes the double acylation of the 3',5'- and 2',5'-hydroxyl of the arabinosyl of Polyphyllin I. However, it is discovered in the in vitro screening tests on the antitumor bioactivity of the compounds obtained, the compounds obtained are evaluated as having null or weak activities (YU Biao et al., Acylated Derivative of Dioscin and Its Producing Process and Use, [P] CN 1322729A, 2001).

The present invention has modified Polyphyllin I by acylating its 5'-arabinofuranosyl. The resulting compound has increased antitumor activity by multiple times as compared with Polyphyllin I, which has never been reported to date in any literature in the world. Thus, compounds of this type are promising to be developed as antitumor medicines available clinically.

SUMMARY OF THE INVENTION

One object of the present invention is to provide novel Polyphyllin I derivatives with 5'-acylated arabinofuranosyl of the following formula (I):

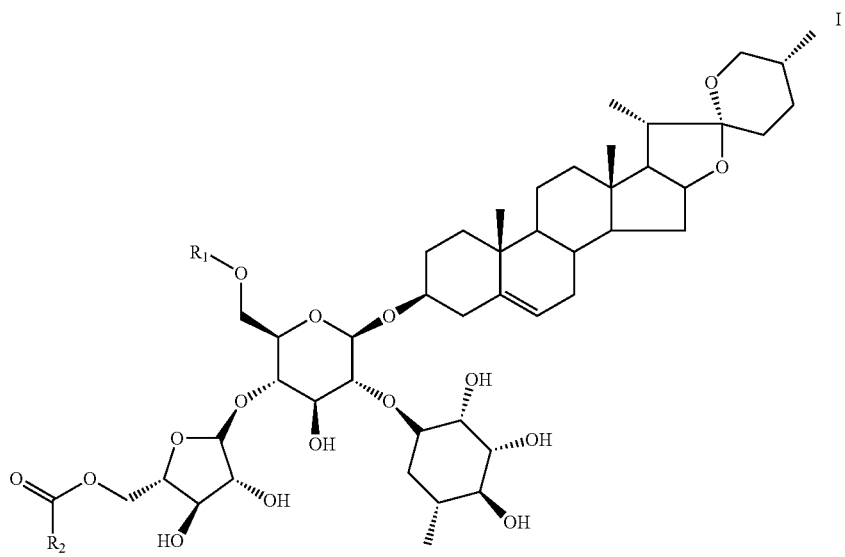

wherein

R₁ is selected from H, substituted or unsubstituted $C_1$-$C_6$ alkyl, substituted or unsubstituted $C_2$-$C_6$ alkenyl, substituted or unsubstituted $C_3$-$C_7$ cycloalkyl, substituted or unsubstituted $C_3$-$C_7$ cycloalkenyl, substituted or unsubstituted aryl $C_1$-$C_6$ alkyl, substituted or unsubstituted heterocyclyl, substituted or unsubstituted heteroaryl, substituted or unsubstituted $C_1$-$C_6$ alkylacyl or substituted or unsubstituted arylacyl;

R₂ is selected from H, substituted or unsubstituted $C_1$-$C_6$ alkyl, substituted or unsubstituted $C_2$-$C_7$ alkenyl, substituted or unsubstituted $C_3$-$C_7$ cycloalkyl, substituted or unsubstituted $C_3$-$C_7$ cycloalkenyl, substituted or unsubstituted aryl, substituted or unsubstituted heterocyclyl, or substituted or unsubstituted heteroaryl;

the substituent in the aforementioned substituted groups is one or more selected from halogen, amino, —$NH_{2-n}(C_1$-$C_6$ alkyl)$_n$, —$NH_{2-n}(C_3$-$C_6$cycloalkyl)$_n$, nitro, cyano, hydroxyl, trifluoromethyl, $C_1$-$C_6$ alkoxy, thiol or $C_1$-$C_6$ alkylthio;

wherein n is an integer selected from 1 or 2;

or a pharmaceutically acceptable adduct, complex or salt thereof.

The second object of the present invention is to provide a process for preparing the Polyphyllin I derivatives of the following formula (I) with 5'-acylated arabinofuranosyl:

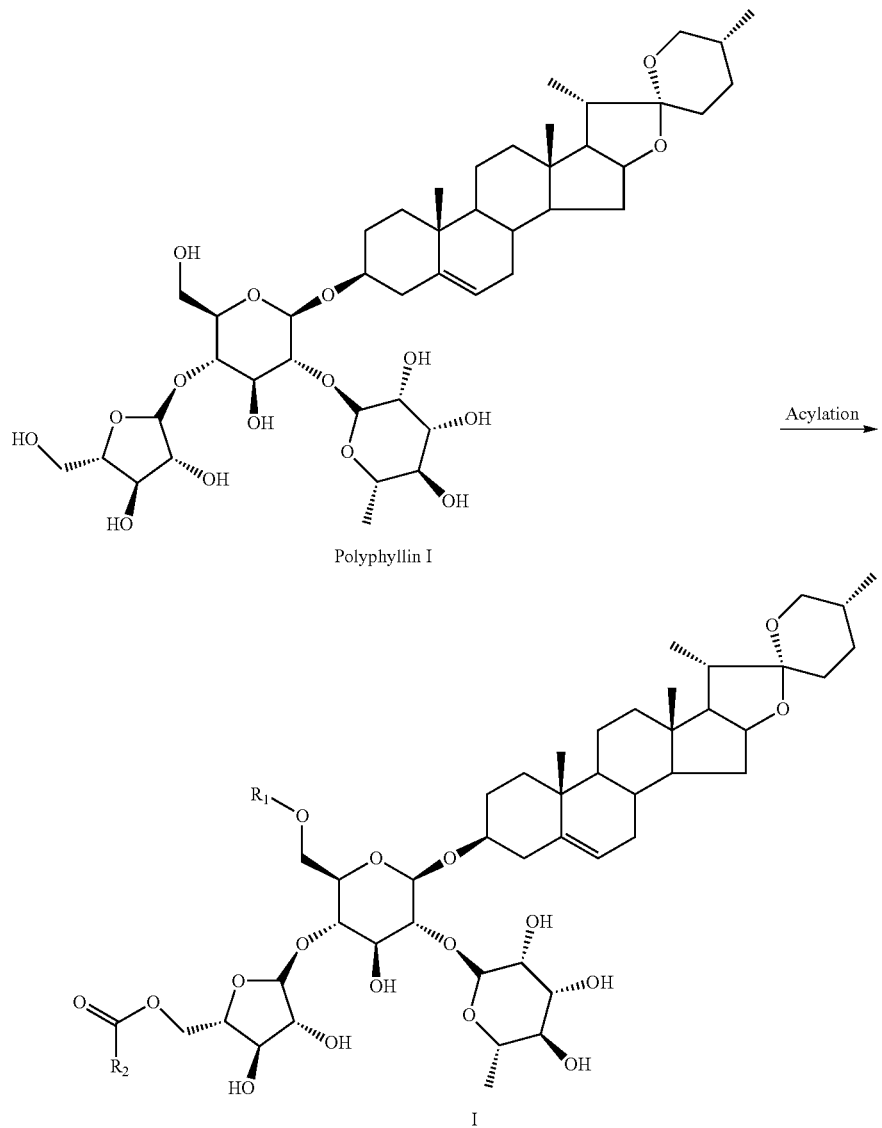

in which the Polyphyllin I derivative with 5'-acylated arabinofuranosyl (corresponding to compound of formula I in which R₁ is H) can be prepared by condensation esterification of naturally extracted Polyphyllin I and the corresponding organic acid $R_2CO_2H$ in the presence of a condensation agent or a catalyst; or by condensation esterification of Polyphyllin I and the corresponding organic acyl chloride $R_2COCl$ or organic anhydride $(R_2CO)_2O$ in the presence of a condensation agent or an alkaline reagent; or by first activating the organic acid $R_2CO_2H$ into an intermediate followed by reacting with Polyphyllin I (formula I, in which $R_1$ is H); or by first activating the hydroxyl in the arabinofuranosyl of Polyphyllin I into an intermediate followed by reacting with the organic acid $R_2CO_2H$ (formula I, in which $R_1$ is H), wherein $R_2$ in formula (I), $R_2$ in the organic acid $R_2CO_2H$, and $R_2$ in the organic acyl chloride $R_2COCl$ are defined as above for formula (I).

The third object of the present invention is to provide a pharmaceutical composition containing the compounds of the present invention, wherein said pharmaceutical composition comprises at least one compound of the present invention and optionally a pharmaceutically acceptable excipient.

The fourth object of the present invention is to provide use of the compound of the present invention or the pharmaceutical composition comprising said compound in the manufacture of a medicament, in particular an antitumor medicament. Accordingly, the present invention also provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor and prostate cancer, etc.

The present invention also relates to the compounds of the present invention used for treating a tumor.

DETAILED DESCRIPTION OF THE INVENTION

The present invention relates to novel Polyphyllin I derivatives of formula (I) with 5'-acylated arabinofuranosyl group, substituted or unsubstituted $C_1$-$C_6$ alkylacyl or substituted or unsubstituted arylacyl;

$R_2$ is selected from H, substituted or unsubstituted $C_1$-$C_6$ alkyl, substituted or unsubstituted $C_2$-$C_7$ alkenyl, substituted or unsubstituted $C_3$-$C_7$ cycloalkyl, substituted or unsubstituted $C_3$-$C_7$ cycloalkenyl, substituted or unsubstituted aryl, substituted or unsubstituted heterocyclyl, or substituted or unsubstituted heteroaryl;

the substituent in the aforementioned substituted groups is one or more selected from halogen, amino, —$NH_{2-n}(C_1$-$C_6$ alkyl$)_n$, —$NH_{2-n}(C_3$-$C_6$cycloalkyl$)_n$, nitro, cyano, hydroxyl, trifluoromethyl, $C_1$-$C_6$ alkoxy, thiol or $C_1$-$C_6$ alkylthio;

wherein n is an integer selected from 1 or 2;

or a pharmaceutically acceptable adduct, complex or salt thereof.

In an embodiment, the present invention relates to a compound of formula (I), wherein $R_1$ is preferably H; $R_2$ is preferably substituted or unsubstituted aryl, in which the aryl is phenyl; and $R_2CO$ is selected from the corresponding organic acid, organic acyl chloride, or organic anhydride.

In an embodiment, the present invention relates to a compound of formula (I), wherein $R_1$ is preferably H; $R_2$ is preferably substituted or unsubstituted heteroaryl, said heteroaryl being a five-membered or six-membered aromatic ring radical containing nitrogen, oxygen or sulfur heteroatoms; the heteroaryl represented by $R_2$ is more preferably selected from furanyl, thienyl, pyridyl, or pyrryl; and $R_2CO$ is selected from the corresponding organic acid, organic acyl chloride, or organic anhydride.

In an embodiment, the present invention relates to a compound of formula (I), wherein $R_1$ is preferably H; $R_2$ is preferably selected from substituted or unsubstituted $C_1$-$C_6$ alkyl, substituted or unsubstituted $C_2$-$C_7$ alkenyl, substituted or unsubstituted $C_3$-$C_7$ cycloalkyl, or substituted or unsubstituted $C_3$-$C_7$ cycloalkenyl; $R_2$ is more preferably selected from cyclopropyl, cyclopentyl, cyclohexyl, cyclopentenyl, cyclohexenyl, methyl, ethyl, propyl, isopropyl, n-butyl, isobutyl, tert-butyl, aminobutyl, arylmethyl, or arylethyl; and $R_2CO$ is selected from the corresponding organic acid, organic acyl chloride, or organic anhydride.

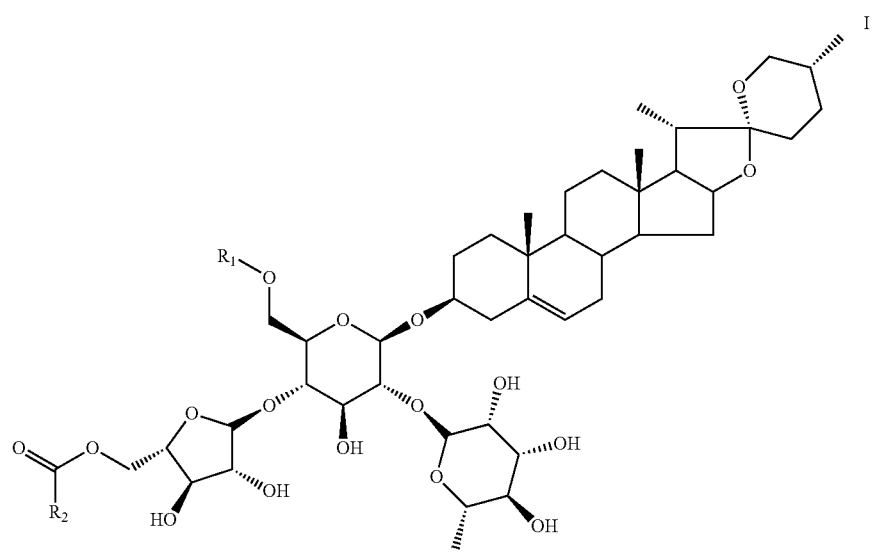

wherein
$R_1$ is selected from H, substituted or unsubstituted $C_1$-$C_6$ alkyl, substituted or unsubstituted $C_2$-$C_6$ alkenyl, substituted or unsubstituted $C_3$-$C_7$ cycloalkyl, substituted or unsubstituted $C_3$-$C_7$ cycloalkenyl, substituted or unsubstituted aryl $C_1$-$C_6$ alkyl, substituted or unsubstituted heterocyclyl, substituted or unsubstituted heteroaryl, In a plurality of embodiments of the present invention, the present invention relates to a compound of formula (I), wherein $R_2$ is preferably substituted with one or more substituents selected from halogen, amino, —$NH_{2-n}(C_1$-$C_6$ alkyl$)_n$, —$NH_{2-n}(C_3$-$C_6$cycloalkyl$)_n$, nitro, cyano, hydroxyl, trifluoromethyl, $C_1$-$C_6$ alkoxy, thiol or $C_1$-$C_6$ alkylthio, wherein n is an integer selected from 1 or 2; said substituent is more preferably fluoro, chloro, bromo, nitro, amino, cyano, methoxyl, ethoxyl, propoxyl, methyl, ethyl, propyl, isopropyl, trifluoromethyl, trifluoromethoxyl, n-butyl, isobutyl, tert-butyl, methylamino, dimethylamino, ethylamino, diethylamino, cyclopropylamino, dicyclopropylamino, methylthio, ethylthio, propylthio, or butylthio; and $R_2CO$ is selected from the corresponding organic acid, organic acyl chloride, or organic anhydride.

Some compounds of the present invention are shown as follows. The compounds listed are for illustrating the present invention only but not for limiting the scope of the present invention in any sense.

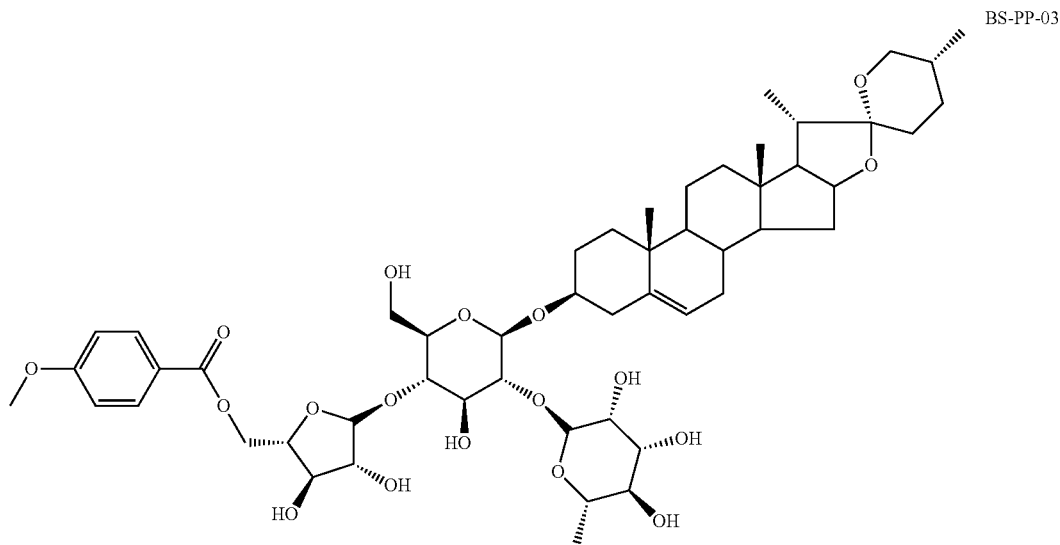

BS-PP-03

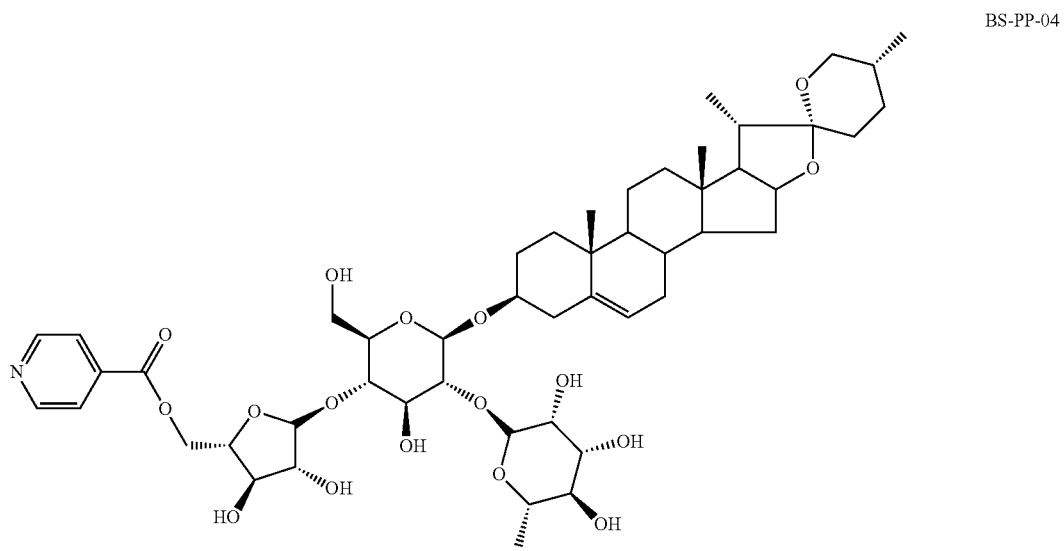

BS-PP-04

-continued
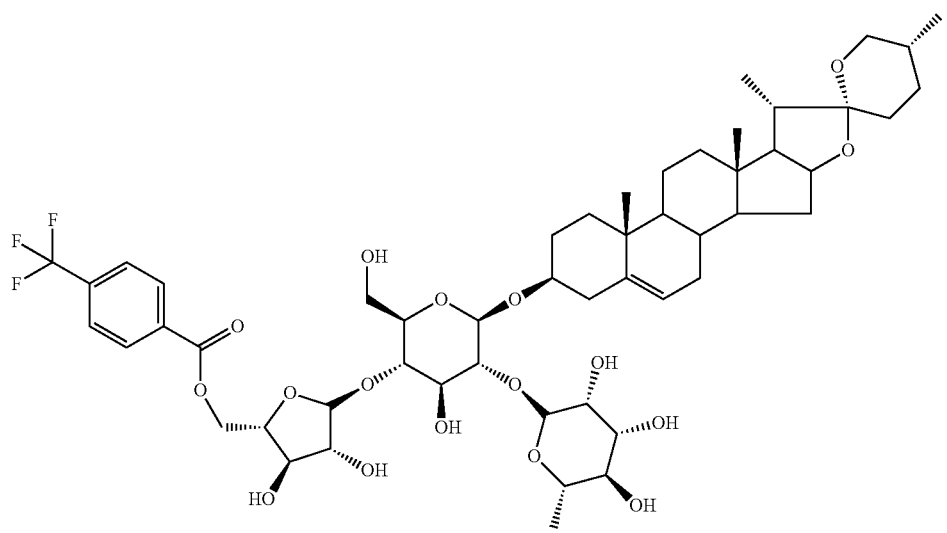
BS-PP-05
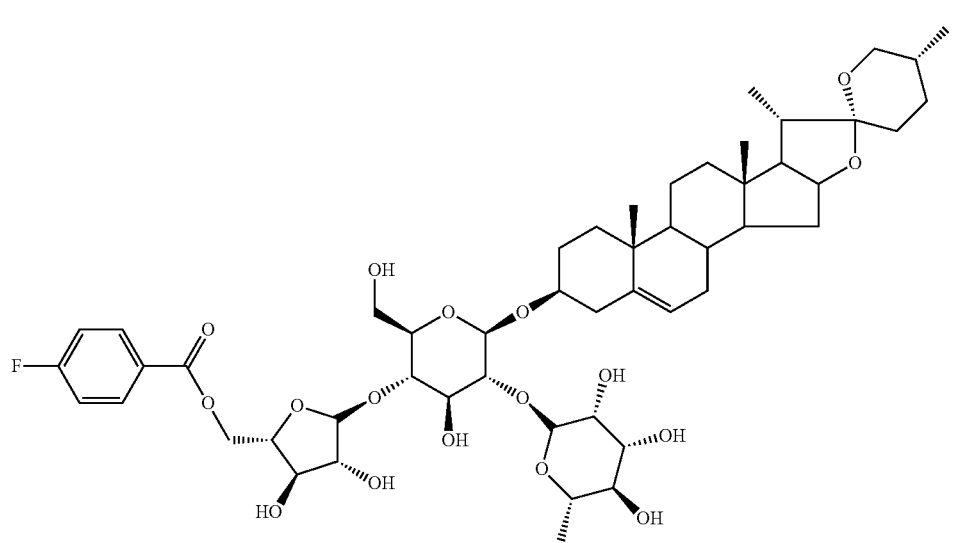
BS-PP-06
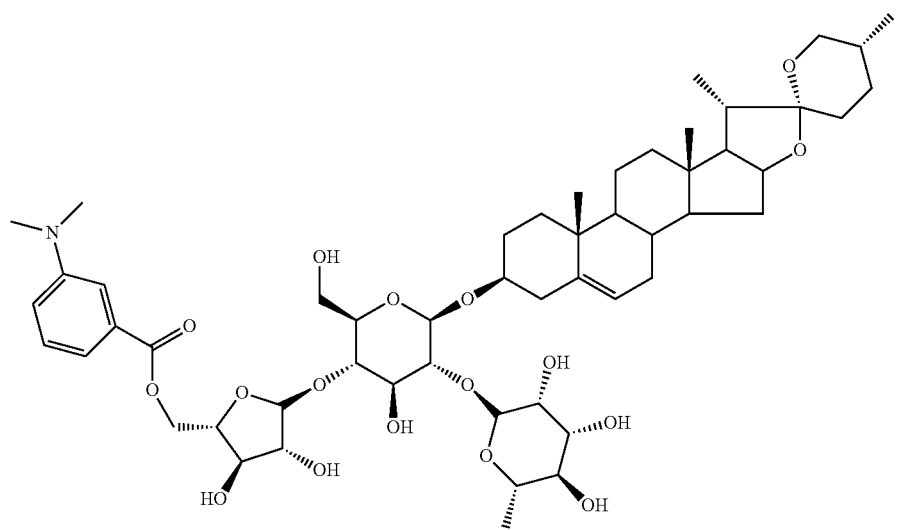
BS-99-07

-continued
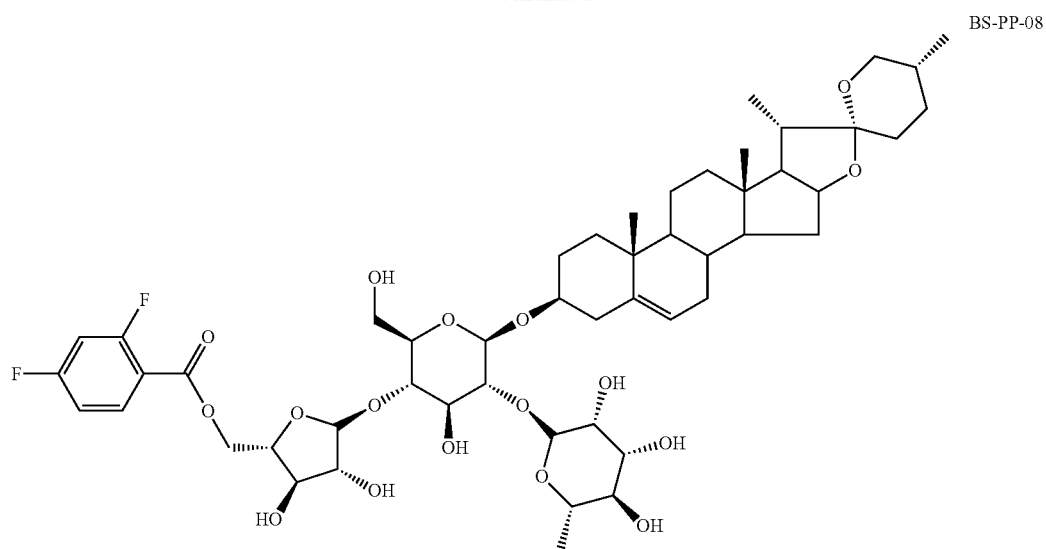
BS-PP-08
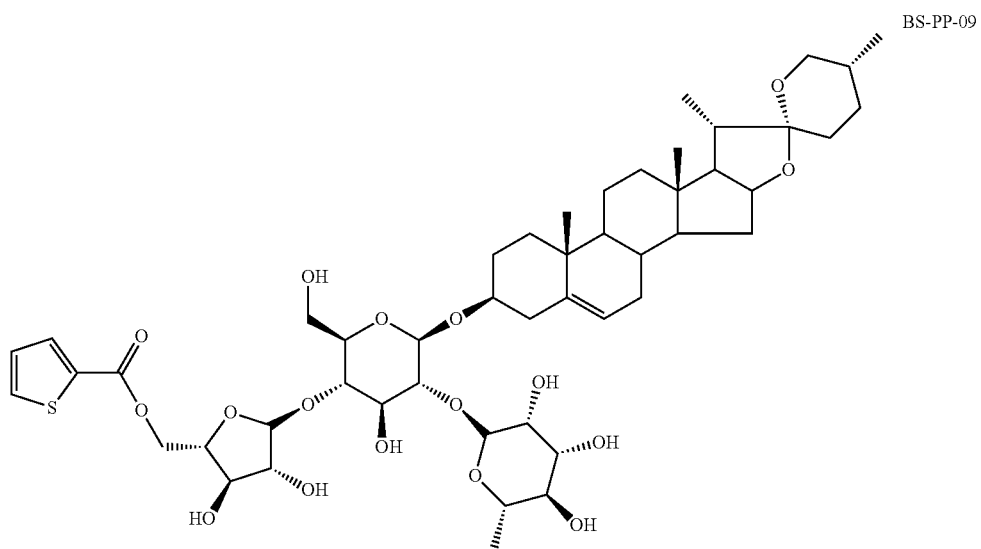
BS-PP-09
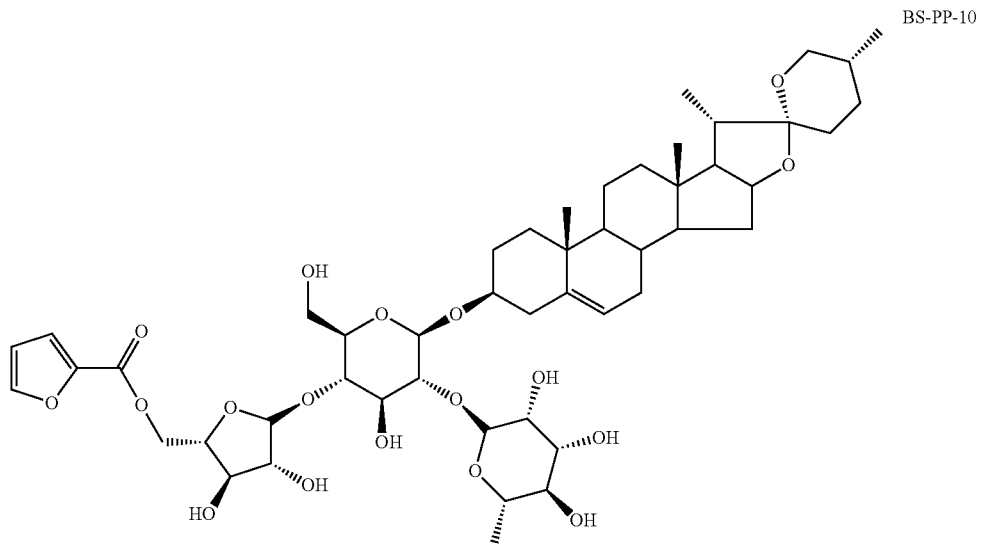
BS-PP-10

-continued
BS-PP-11
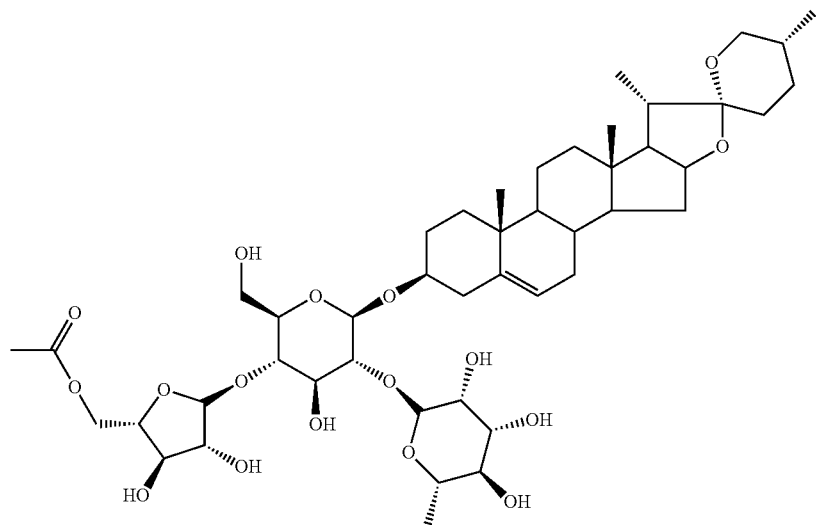
BS-PP-12
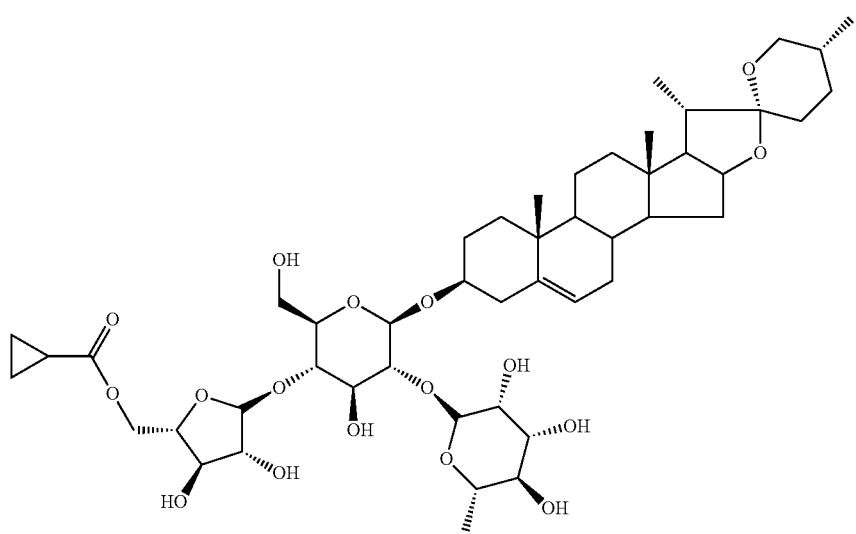
BS-PP-15
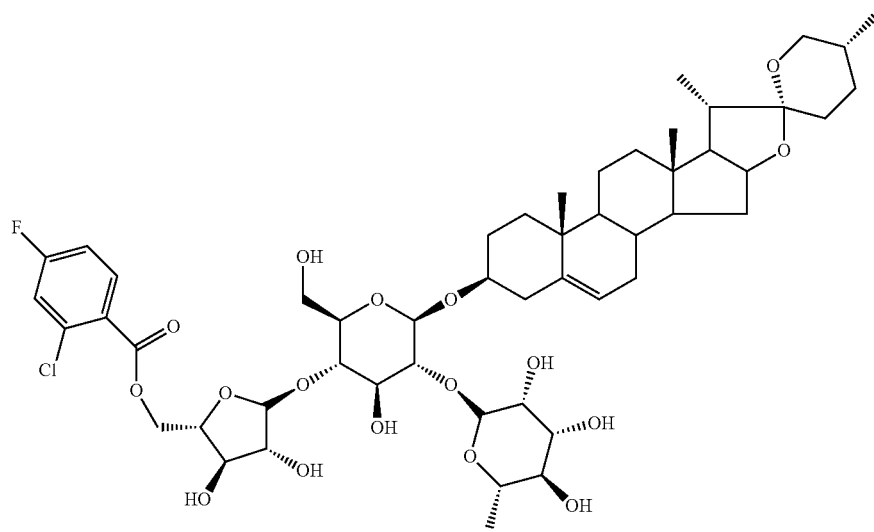

Some data for the compounds shown above are listed in the following table:

| Compound No. | Formula | Molecular Weight | Appearance | State | Total Reaction Yield (%) |
|---|---|---|---|---|---|
| BS-PP-03 | $C_{52}H_{76}O_{18}$ | 989.15 | Off-white | Powdery solid | 15 |
| BS-PP-04 | $C_{50}H_{73}NO_{17}$ | 960.11 | Off-white | Powdery solid | 9.1 |
| BS-PP-05 | $C_{52}H_{73}F_{3}O_{17}$ | 1027.12 | Off-white | Powdery solid | 7 |
| BS-PP-06 | $C_{51}H_{73}FO_{17}$ | 977.11 | Off-white | Powdery solid | 10 |
| BS-PP-07 | $C_{53}H_{79}NO_{17}$ | 1002.19 | Off-white | Powdery solid | 12 |
| BS-PP-08 | $C_{51}H_{72}F_{2}O_{17}$ | 995.1 | Off-white | Powdery solid | 9 |
| BS-PP-09 | $C_{49}H_{72}O_{17}S$ | 965.15 | Off-white | Powdery solid | 8.6 |
| BS-PP-10 | $C_{49}H_{72}O_{18}$ | 949.09 | Off-white | Powdery solid | 16 |
| BS-PP-11 | $C_{46}H_{72}O_{17}$ | 897.05 | Off-white | Powdery solid | 15 |
| BS-PP-12 | $C_{48}H_{74}O_{17}$ | 923.09 | Off-white | Powdery solid | 11 |
| BS-PP-15 | $C_{51}H_{72}ClFO_{17}$ | 1011.56 | Off-white | Powdery solid | 5.6 |

According to another embodiment of the present invention, the following compounds of formula (I) are particularly preferred:

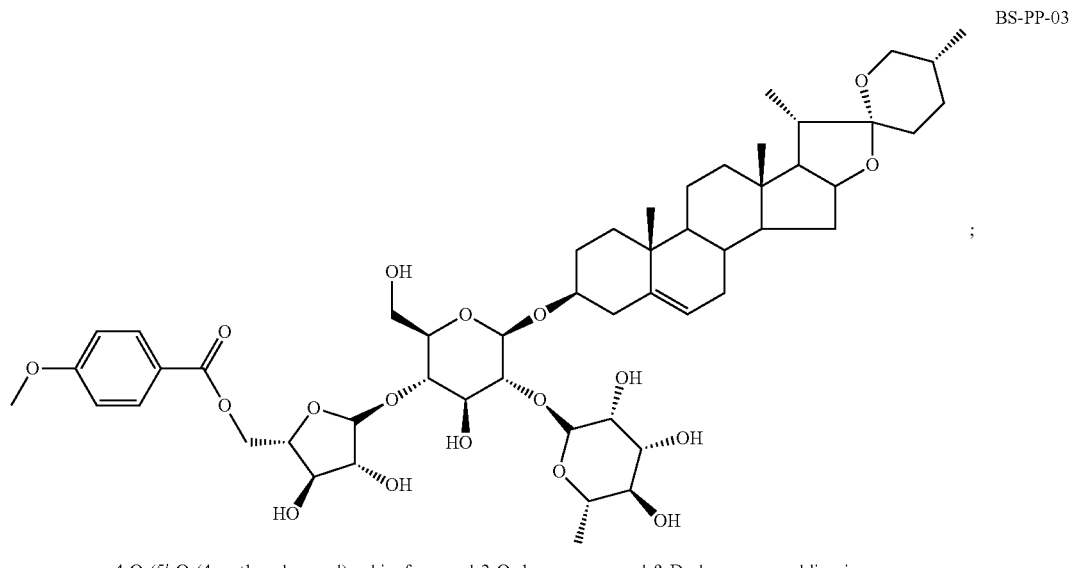

4-O-(5'-O-(4-methoxybenzoyl)arabinofuranosyl-2-O-rhamnopyranosyl-β-D-glucopyranosyldioscin

BS-PP-03

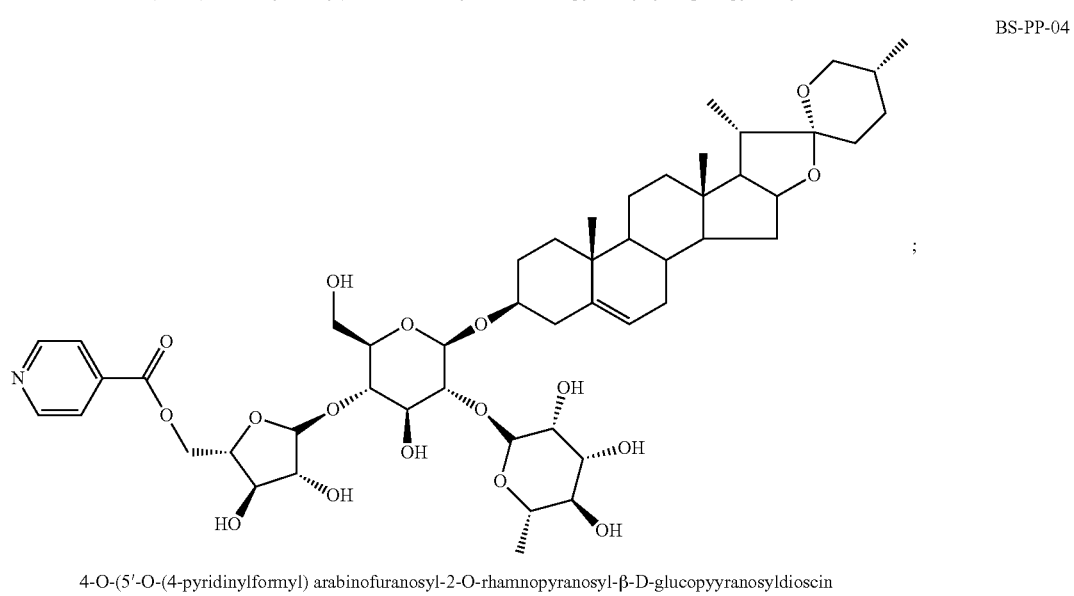

4-O-(5'-O-(4-pyridinylformyl) arabinofuranosyl-2-O-rhamnopyranosyl-β-D-glucopyyranosyldioscin

BS-PP-04

-continued
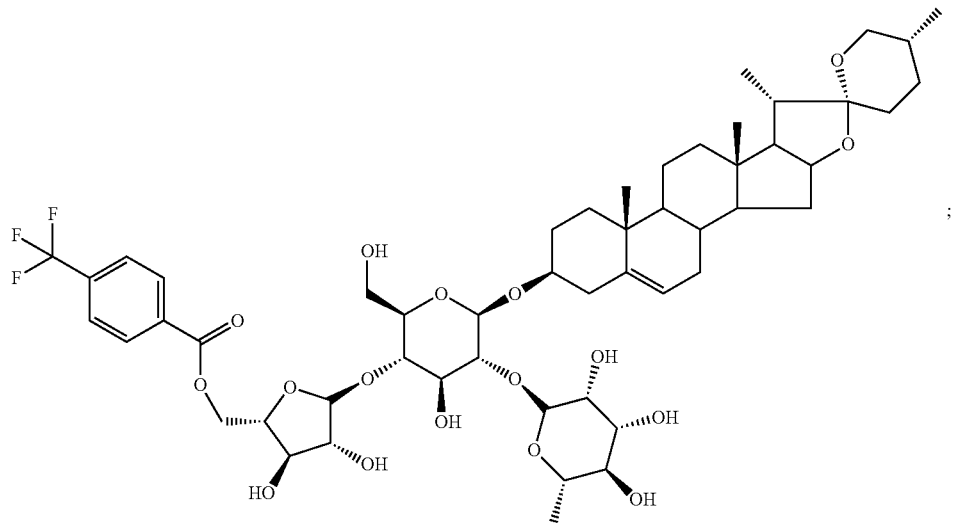
4-O-(5'-O-(4-trifluoromethylbenzoyl)
arabinofuranosyl-2-O-rhamnopyranosyl-β-D-glucopyranosyldioscin
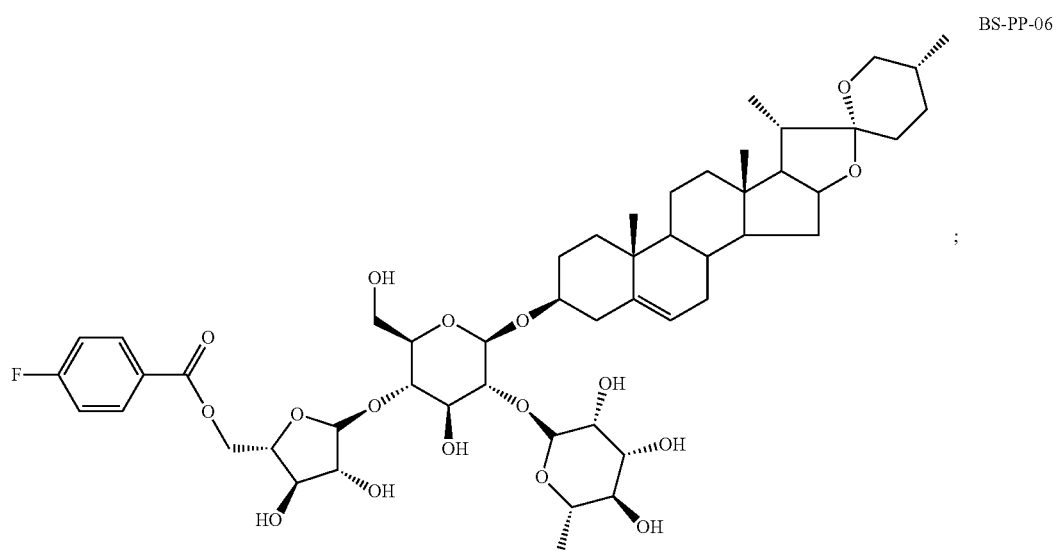
4-O-(5'-O-(4-fluorobenzoyl) arabinofuranosyl-2-O-rhamnopyranosyl-β-D-glucopyranosyldioscin

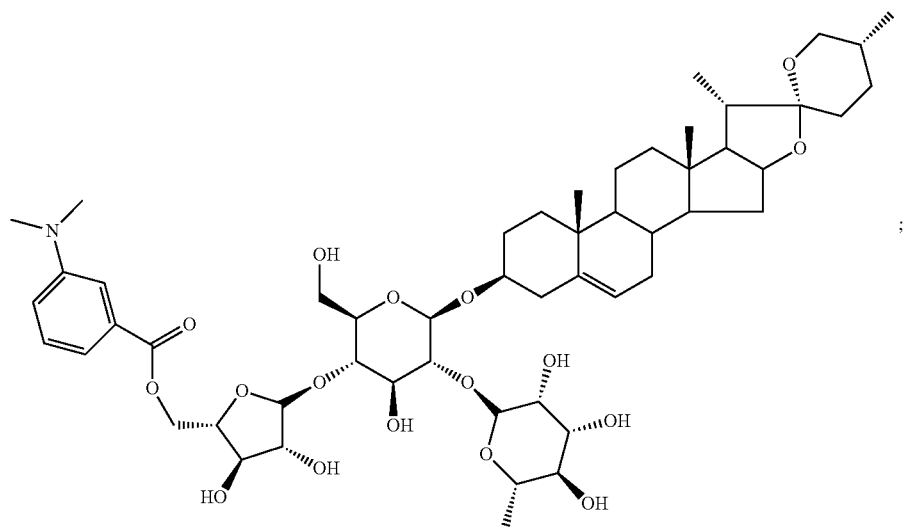
4-O-(5'-O-(4-dimethylaminobenzoyl) arabinofuranosyl-2-O-rhamnopyranosyl-β-D-glucopyranosyldioscin
BS-PP-07
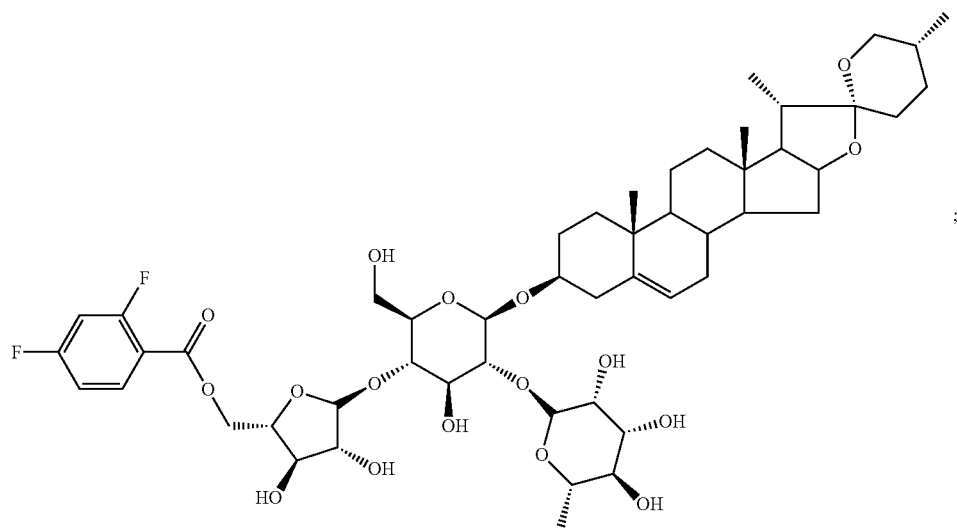
4-O-(5'-O-(2,4-difluorobenzoyl) arabinofuranosyyl-2-O-rhamnopyranosyl-β-D-glucopyranosyldioscin
BS-PP-08

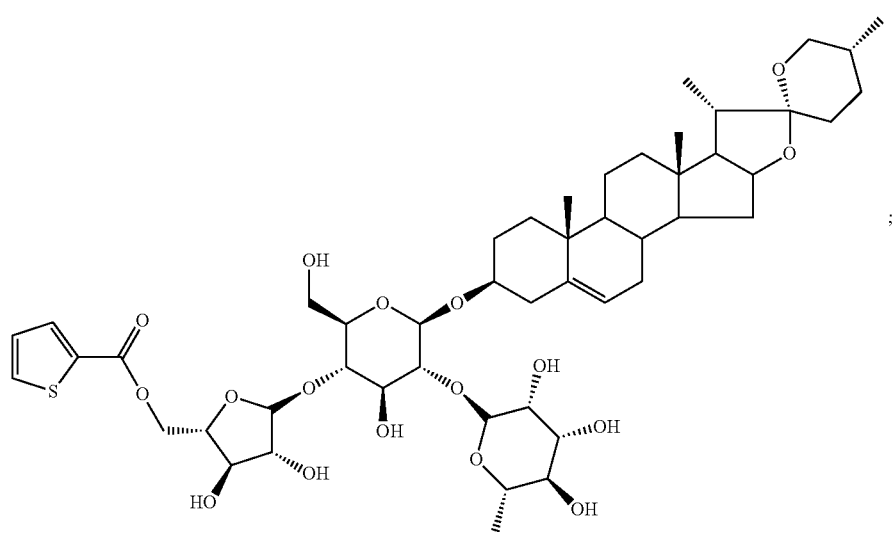
4-O-(5'-O-(2-thiopheneformyl) arabinofuranosyl-2-O-rhamnopyranosyl-β-D-glucoyranosyldioscin
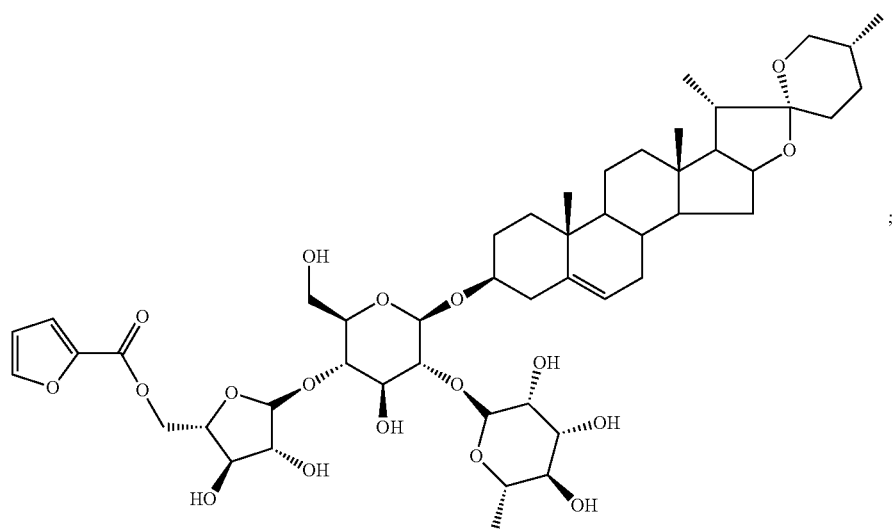
4-O-(5'-O-(2-furanylformyl) arabinofuranosyl-2-O-rhamnoyranosyl-β-D-glucopyranosyldioscin

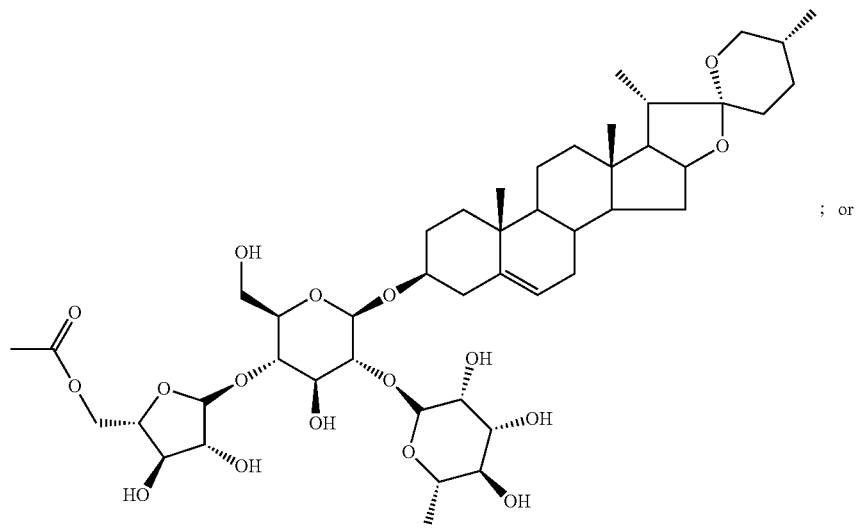
4-O-(5′-O-acetyl) arabinofuranosyl-2-O-rhamnopyranosyl-β-D-glucopyranosyldioscin
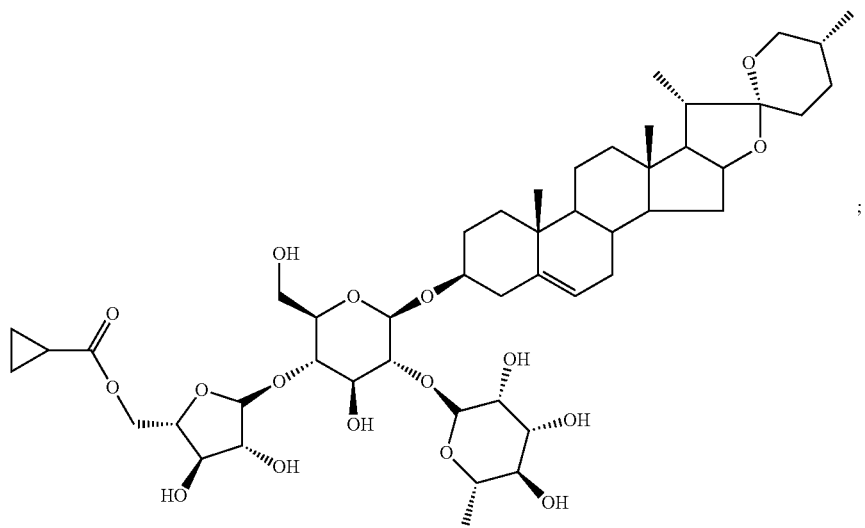
4-O-(5′-O-cyclopropylformyl) arabinofuranosyl-2-O-rhamnoyranosyl-β-D-glucopyranosyldioscin

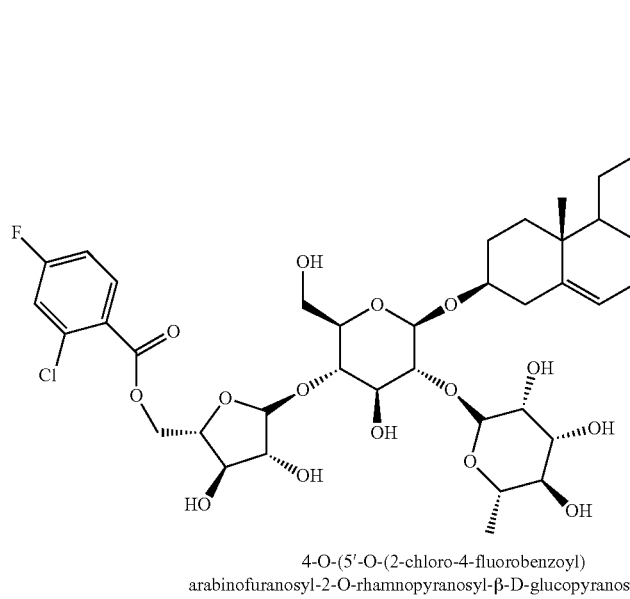

BS-PP-15

4-O-(5'-O-(2-chloro-4-fluorobenzoyl)
arabinofuranosyl-2-O-rhamnopyranosyl-β-D-glucopyranosyldioscin The present invention relates to salts, solvates, hydrates, adducts, complexes, polymorphs or prodrugs of the inventive compounds of formula (I).

As used herein, the term "$C_1$-$C_6$ alkyl" refers to a straight or branched, substituted or unsubstituted hydrocarbon radical containing 1-6 carbon atoms. Examples of $C_1$-$C_6$ alkyl include, but not limited to, methyl, ethyl, n-propyl, isopropyl, tert-butyl, n-pentyl, n-hexyl, and n-eicosyl.

The term "$C_2$-$C_6$ alkenyl" refers to a straight or branched, substituted or unsubstituted alkenyl radical containing 2-6 carbon atoms. Examples of $C_2$-$C_6$ alkenyl include, but not limited to, vinyl, allyl and eicosenyl.

The term "$C_4$-$C_8$ conjugated alkenyl" refers to a straight or branched, substituted or unsubstituted conjugated alkenyl radical containing 4-8 carbon atoms. Examples of $C_4$-$C_{20}$ conjugated alkenyl include, but not limited to, conjugated butadienyl.

The term "$C_3$-$C_7$ cycloalkyl" or "$C_3$-$C_7$ cycloalkenyl" refers to a saturated or unsaturated 3-7 membered monocyclic hydrocarbon radical. $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl $C_1$-$C_6$ alkyl" refers to an aryl $C_1$-$C_6$ alkyl radical having no heteroatoms.

The term "aryl" refers to a monocyclic aryl or polycyclic aryl, fused or unfused, containing 6-14 (such as 6-12 or 6-20) carbon atoms. In the case of polycyclic aryl, at least one ring is aromatic. Aryl can also be one fused with a heterocyclic radical. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring member(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

The term "heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclic radical can be a monocyclic heterocyclic radical having 4-8 (such as 4-7, 5-7) ring atoms or a bicyclic heterocyclic radical having 7-11 ring atoms. A heterocyclic radical can be aromatic or non-aromatic. Examples of heterocyclic radicals include azacyclobutyl, pyrrolidinyl, pyrrolinyl, tetrahydrofuranyl, dihydrofuranyl, piperazinyl, piperidinyl, morpholinyl, thiomorpholinyl, tetrahydropyranyl, tetrahydrothiophenyl, etc.

The term "amino acid" refers to natural amino acids and unnatural amino acids.

The term "halogen" refers to fluorine, chlorine, bromine or iodine.

The term "$C_1$-$C_6$ alkoxy" refers to —O—$C_1$-$C_6$ alkyl and —O—$C_3$-$C_6$ cycloalkyl.

The term "$C_1$-$C_6$ alkylthio" refers to —S—$C_1$-$C_6$ alkyl and —S—$C_3$-$C_6$ cycloalkyl.

The term "pharmaceutically acceptable adducts, or complexes of the compounds of formula (I)" refers to the product formed by a compound of the present invention with further combined small molecule or biological macromolecule via a non-chemical bond or non-covalent intermolecular force.

As used herein, the term "pharmaceutically acceptable salts of the compounds of formula (I)" refers to the organic acid salts formed by the compounds of the present invention with an organic acid which comprises a pharmaceutically acceptable anion. These organic acid salts include, but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in *Burger's Medicinal Chemistry and Drug Discovery* (1995) 172-178, 949-982 (Manfred E. Wolff, 5th edition), *Prodrugs and Targeted Delivery* by J. Rautio (2011) 31-60 (Wiley-VCH, *Methods and Principles in Medicinal Chemistry*, Vol. 47), and *Fundamentals of Medicinal Chemistry* (2003) by G. Thomas, 195-200 (Wiley).

In the compounds of the present invention, the Polyphyllin I derivatives with 5'-acylated arabinofuranosyl have 25 chiral centers in the stereochemical structure, as represented by the structural formula I. The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is typically prepared as follows.

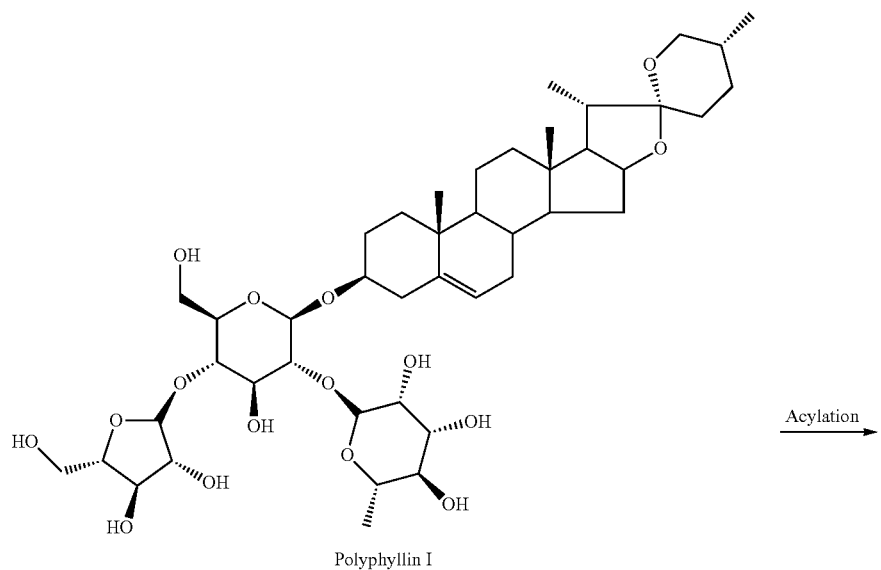

Polyphyllin I

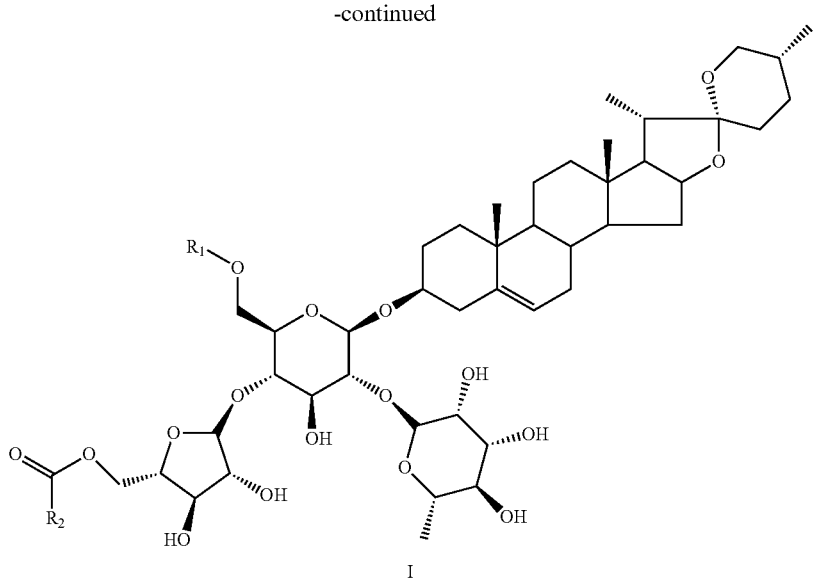

I

The Polyphyllin I derivatives with 5'-acylated arabinofuranosyl (corresponding to compound of formula I in which $R_1$ is H) can be prepared
- by the condensation esterification of naturally extracted Polyphyllin I and the corresponding organic acid $R_2CO_2H$, organic acyl chloride $R_2COCl$ or organic anhydride $(R_2CO)_2O$; or
- by first activating the organic acid $R_2CO_2H$ into an intermediate followed by reacting with Polyphyllin I (formula I, in which $R_1$ is H); or
- by first activating the hydroxyl of arabinofuranosyl of Polyphyllin I into an intermediate followed by reacting with the organic acid $R_2CO_2H$ (formula I, in which $R_1$ is H), wherein $R_2$ in formula (I) is defined as above for formula (I).

The above reaction is typically carried out in the presence of an alkali or an alkaline reagent. The alkali herein can be, but not limited to, an organic alkali, such as diisopropylethylamine, triethylamine, or dimethylaminopyridine.

The above reaction typically is carried out in a solution. The solvents used herein include, but not limited to, aprotic polar solvents, such as dichloromethane (DCM), dimethylsulfoxide (DMSO), dimethylformamide (DMF) or tetrahydrofuran (THF) etc.

The above reaction typically takes place at a temperature of 0° C.-50° C., which generally varies with the raw material and the alkali used.

The raw material for the preparation reaction is Polyphyllin I, which is obtained by extraction from natural products and is also commercially available.

The organic acids, organic anhydrides or organic acyl chlorides for the preparation reaction are commercially available.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups* in Organic Synthesis, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally or parenterally (for example, by an intravenous, intramuscular, topical or subcutaneous route).

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The Polyphyllin I derivative with 5'-acylated arabinofuranosyl groups of the present invention or a pharmaceutically acceptable salt thereof can be used for the treatment of numerous tumors, for example, leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detail by the following examples. However, it should be understood that the following examples are intended for illustration only but not to limit the scope of the present invention in any way.

The raw chemicals used in the following examples are commercially available or may be obtained by a synthesis method known in the art.

Example 1

Synthesis of Compound BS-PP-10

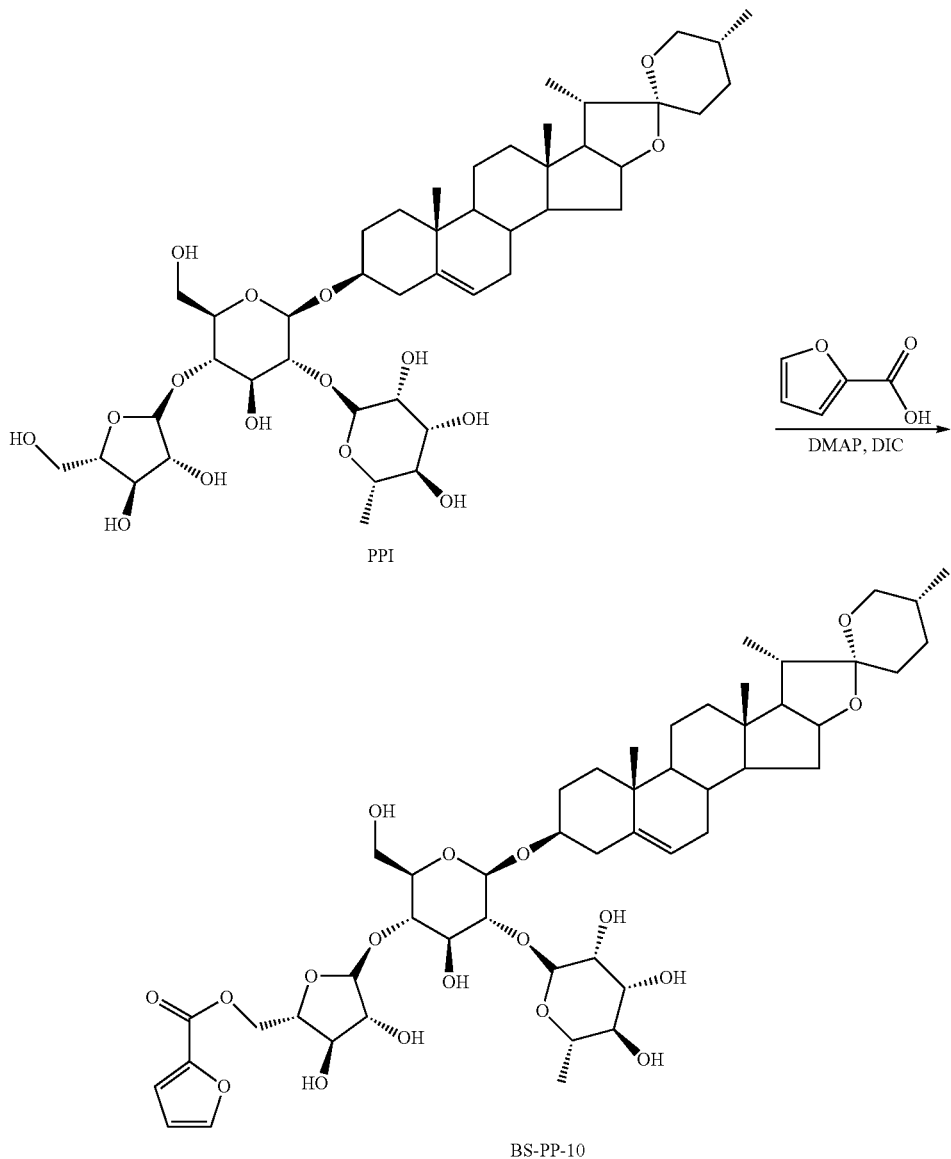

wherein, DMAP: 4-dimethylaminopyridine; DIC: N,N'-diisopropylcarbodiimide.

Polyphyllin I (250 mg, 0.2924 mmol) is added to a tetrahydrofuran (4 mL) solution, followed by the addition of 2-furoic acid (36 mg, 0.2924 mmol) and 4-dimethylaminopyridine (7 mg, 0.0585 mmol). After the system is cooled down to 0° C., N,N'-diisopropylcarbodiimide (36.3 mg, 0.23 mmol) is added dropwise and the reaction solution is stirred for 2 hours at room temperature. After the reaction completes, the reaction solution is concentrated, separated by silica gel column chromatography (DCM:MeOH=50:1) and then purified by preparative thin layer chromatography (DCM:MeOH=20:1) to give the compound BS-PP-10 (32.2 mg, yield: 11%) as an off-white powdery solid.

LC-MS (ELSD): retention time: 1.47 min (96.16%); m/z 972.3 (M+Na).

$^1$H NMR (301 MHz, partial assignment of signals in CD$_3$OD) δ 7.58 (dd, J=1.8, 0.9 Hz, 1H), 7.20 (dd, J=3.6, 0.9 Hz, 1H), 6.52 (dd, J=3.3, 1.5 Hz, 1H), 5.28 (s, 1H), 5.17 (d, J=1.5 Hz, 1H), 4.96 (d, J=2.1 Hz, 1H), 4.33 (s, 1H), 4.31 (d, J=7.5 Hz, 1H), 4.22 (d, 2H), 4.05-3.97 (m, 3H), 3.87-3.83 (m, 2H), 2.31 (m, 1H), 2.20 (m, 1H), 1.17 (d, J=6.0 Hz, 3H), 0.94 (s, 3H), 0.88 (d, J=6.9 Hz, 3H), 0.71 (d, J=4.2 Hz, 6H).

BS-PP-03 is prepared according to the process for BS-PP-10 using the same alkaline reagents and solvents by reacting Polyphyllin I with p-methoxybenzoic acid.

BS-PP-03: LC-MS (ELSD): retention time: 1.56 min (98.61%), m/z 989.15.

$^1$H NMR (301 MHz, partial assignment of signals in CD$_3$OD) δ 8.03 (d, J=9 Hz, 2H), 7.01 (d, J=8.7 Hz, 2H), 5.34 (d, J=4.5 Hz, 1H), 5.30 (s, 1H), 5.08 (d, J=1.8 Hz, 1H), 4.16-4.08 (m, 3H), 4.00-3.97 (m, 2H), 2.44 (m, 1H), 2.33 (m, 1H), 1.27 (d, J=6.0 Hz, 6H), 1.03 (s, 3H), 0.97 (d, J=6.0 Hz, 4H), 0.80 (d, 7H).

BS-PP-04 is prepared according to the process for BS-PP-10 using the same alkaline reagents and solvents by reacting Polyphyllin I with isonicotinic acid.

BS-PP-04: LC-MS (ELSD): retention time: 1.30 min (97.7%), m/z 961.5 (M+H), 481.0 (½M+H).

$^1$H NMR (301 MHz, partial assignment of signals in $CD_3OD$) δ 8.79 (s, 2H), 7.99 (d, J=3.6 Hz, 2H), 5.38 (d, J=4.8 Hz, 1H), 5.30 (s, 1H), 5.07 (d, J=1.8 Hz, 1H), 2.41 (m, 1H), 2.29 (m, 1H), 1.29 (d, J=5.4 Hz, 6H), 1.04 (s, 3H), 0.99 (d, J=6.9 Hz, 4H), 0.81 (d, 7H).

BS-PP-05 is prepared according to the process for BS-PP-10 using the same alkaline reagents and solvents by reacting Polyphyllin I with 4-(trifluoromethyl)benzoic acid.

BS-PP-05: LC-MS (ELSD): retention time: 1.67 min (99.01%), m/z 1027.12.

$^1$H NMR (301 MHz, partial assignment of signals in $CD_3OD$) δ 8.23 (d, J=8.4 Hz, 2H), 7.81 (d, J=8.4 Hz, 2H), 5.37 (d, J=4.2 Hz, 1H), 5.29 (s, 1H), 5.09 (d, J=2.1 Hz, 1H), 4.15-3.95 (m, 5H), 2.41 (m, 1H), 2.29 (m, 1H), 1.29 (d, J=6 Hz, 6H), 1.03 (s, 3H), 0.99 (d, J=6.9 Hz, 4H), 0.82 (d, 7H).

BS-PP-06 is prepared according to the process for BS-PP-10 using the same alkaline reagents and solvents by reacting Polyphyllin I with p-fluorobenzoic acid.

BS-PP-06: LC-MS (ELSD): retention time: 1.56 min (91.34%), m/z 977.3.

$^1$H NMR (301 MHz, partial assignment of signals in $CD_3OD$) δ 8.12 (dd, J=9 Hz, 5.4 Hz, 2H), 7.20 (t, J=8.7 Hz, 2H), 5.38 (d, J=5.7 Hz, 1H), 5.28 (s, 1H), 5.06 (d, J=2.1 Hz, 1H), 4.15-4.07 (m, 3H), 3.95 (m, 6H), 2.40 (m, 1H), 2.32 (m, 1H), 1.29 (d, J=6.0 Hz, 6H), 1.03 (s, 3H), 0.99 (d, J=6.9 Hz, 4H), 0.80 (d, 7H).

BS-PP-07 is prepared according to the process for BS-PP-10 using the same alkaline reagents and solvents by reacting Polyphyllin I with m-dimethylaminobenzoic acid.

BS-PP-07: LC-MS (ELSD): retention time: 1.37 min (99.21%), m/z 1003.4 (M+H), 502.0 (½M+H).

$^1$H NMR (301 MHz, partial assignment of signals in $CD_3OD$) δ 7.41 (m, 2H), 7.34 (t, J=2.1 Hz, 1H), 6.96 (dd, J=8.1 Hz, 2.7 Hz, 1H), 5.37 (d, J=4.8 Hz, 1H), 5.24 (s, 1H), 5.08 (d, J=2.1 Hz, 1H), 2.99 (s, 6H), 2.49 (m, 1H), 2.28 (m, 1H), 1.28 (d, J=6.0 Hz, 6H), 1.03 (s, 3H), 0.99 (d, J=6.9 Hz, 4H), 0.78 (d, 7H).

BS-PP-08 is prepared according to the process for BS-PP-10 using the same alkaline reagents and solvents by reacting Polyphyllin I with 2,4-difluorobenzoic acid.

BS-PP-08: LC-MS (ELSD): retention time: 1.57 min (98.87%), m/z 1018.3 (M+Na).

$^1$H NMR (301 MHz, partial assignment of signals in $CD_3OD$) δ 8.00 (m, 1H), 7.00 (m, 1H), 6.92 (m, 1H), 5.31 (d, J=5.1 Hz, 1H), 5.22 (s, 1H), 5.01 (d, J=2.4 Hz, 1H), 2.35 (m, 1H), 2.25 (m, 1H), 1.24 (d, J=6.3 Hz, 6H), 0.98 (s, 3H), 0.92 (d, J=6.9 Hz, 4H), 0.75 (d, 7H).

BS-PP-09 is prepared according to the process for BS-PP-10 using the same alkaline reagents and solvents by reacting Polyphyllin I with 2-thiophenecarboxylic acid.

BS-PP-09: LC-MS (ELSD): retention time: 1.53 min (99.01%), m/z 965.1.

$^1$H NMR (301 MHz, partial assignment of signals in $CD_3OD$) δ 7.87 (dd, J=3.6 Hz, 1.2 Hz, 1H), 7.66 (dd, J=5.1 Hz, 1.2 Hz, 1H), 7.17 (m, 1H), 5.37 (d, J=5.1 Hz, 1H), 5.28 (s, 1H), 5.05 (d, J=2.1 Hz, 1H), 2.40 (m, 1H), 2.29 (m, 1H), 1.27 (d, J=6.3 Hz, 6H), 1.03 (s, 3H), 0.99 (d, J=6.9 Hz, 4H), 0.80 (d, 7H).

BS-PP-11 is prepared according to the process for BS-PP-10 using the same alkaline reagents and solvents by reacting Polyphyllin I with acetic acid.

BS-PP-11: LC-MS (ELSD): retention time: 1.39 min (97.77%), m/z 897.3.

$^1$H NMR (301 MHz, partial assignment of signals in $CD_3OD$) δ 5.36 (d, J=4.5 Hz, 1H), 5.24 (s, 1H), 5.03 (d, J=2.1 Hz, 1H), 2.40 (m, 1H), 2.33 (m, 1H), 2.10 (s, 3H), 1.28 (d, J=6.0 Hz, 6H), 1.04 (s, 3H), 0.99 (d, J=6.9 Hz, 4H), 0.81 (d, 7H).

BS-PP-12 is prepared according to the process for BS-PP-10 using the same alkaline reagents and solvents by reacting Polyphyllin I with cyclopropaneformic acid.

BS-PP-12: LC-MS (ELSD): retention time: 1.45 min (99.44%), m/z 946.4 (M+Na).

$^1$H NMR (301 MHz, partial assignment of signals in $CD_3OD$) δ 5.37 (d, J=4.8 Hz, 1H), 5.25 (s, 1H), 5.04 (d, J=2.1 Hz, 1H), 2.40 (m, 1H), 2.29 (m, 1H), 1.29 (d, J=6.3 Hz, 6H), 1.03 (s, 3H), 0.99 (d, J=6.9 Hz, 4H), 0.80 (d, 7H).

BS-PP-15 is prepared according to the process for BS-PP-10 using the same alkaline reagents and solvents by reacting Polyphyllin I with 2-chloro-4-fluorobenzoic acid.

BS-PP-15: LC-MS (ELSD): retention time: 1.61 min (99.10%), m/z 1011.2.

$^1$H NMR (301 MHz, partial assignment of signals in $CD_3OD$) δ 8.02 (m, 1H), 7.25 (dd, J=8.4 Hz, 2.4 Hz, 1H), 7.14 (m, 1H), 5.37 (d, J=4.5 Hz, 1H), 5.26 (s, 1H), 5.07 (d, J=2.1 Hz, 1H), 2.39 (m, 1H), 2.28 (m, 1H), 1.29 (d, J=6.0 Hz, 6H), 1.02 (s, 3H), 0.99 (d, J=6.6 Hz, 4H), 0.79 (d, 7H).

Example 2

Evaluation of the Polyphyllin I Derivatives with 5'-Acylated Arabinofuranosyl Groups of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), and Kasumi-1 (acute myeloid leukemia M2 type, AML-M2), all of which were donated by Cancer Research Institute of Zhejiang University, China.

Reagents: The standard sample of Polyphyllin I (PPI) is purchased from Chengdu Must Bio-Technology Co., Ltd., China; the Polyphyllin I derivatives of the present invention.

Main apparatuses: a Thermo Scientific 3111 incubator and a Bio-Rad iMark microplate reader.

(2) Experimental Method 6000 well-growing leukemia cells were obtained and inoculated into wells of a 96-well cell culture plate. The culture medium used was the 1640 cell culture medium containing 10% fetal bovine serum. After adding the Polyphyllin I derivatives with 5'-acylated arabinofuranosyl of different concentrations and mixing uniformly, the plate was placed in a carbon dioxide cell incubator (5% $CO_2$) at 37° C. and incubated for 72 hours. Then the viable cell concentration was determined by the MTT method. In this experiment, the cell viability in control group (not treated with any compound) is set as 100%. On such basis, the cell viability (%) after treatment of the compound and the 50% inhibiting concentration for the leukemia cell growth at 72 hours ($IC_{50}$ value and $IC_{90}$ value of 72 hours) were calculated.

(3) The Experimental Results

The experimental results are shown in table 1. Table 1 shows that the 5'-acylated arabinofuranosyl Polyphyllin I derivatives of the present invention can induce the death of human chronic myeloid leukemia cells, acute myeloid leukemia cells and acute lymphocytic leukemia cells, and inhibit the growth of these leukemia cells. Compared with Polyphyllin I itself, the Polyphyllin I derivatives with 5'-acylated arabinofuranosyl group of the present invention exhibit significantly enhanced anti-leukemia cell activities. Specifically, the Polyphyllin I derivatives of the present invention BS-PP-04, BS-PP-08, BS-PP-10, BS-PP-11, and BS-PP-12 exhibit particularly significant activities and improve the anti-K562/adr (drug-resistant, chronic myeloid leukemia, CML) activity by more than 2-fold. In addition, BS-PP-04, BS-PP-06, BS-PP-08, BS-PP-10, and BS-PP-11 also improve the anti-NB4 (acute promyelocytic leukemia, AML) and anti-H9 (acute lymphoblastic leukemia, ALL) activities by more than 2-fold.

TABLE 1

Determination of the inhibiting concentrations of the 5'-acylated arabinofuranosyl Polyphyllin I derivatives on the growth of leukemia cells, human multiple myeloma and lymphoma cells (72 h, $IC_{50}$ (µg/mL) value and $IC_{90}$ (µg/mL) value).

| Compounds | K562/adr | | Kasumi-1 |
| --- | --- | --- | --- |
| | $IC_{50}$ | $IC_{90}$ | $IC_{50}$ |
| PP | 0.87 | 2.98 | 0.92 |
| BS-PP-03 | 0.69 | | |
| BS-PP-04 | 0.38 | 2.33 | |
| BS-PP-06 | 0.73 | 2.66 | |
| BS-PP-08 | 0.49 | 2.5 | |
| BS-PP-10 | 0.45 | 2.23 | 0.78 |
| BS-PP-11 | 0.42 | 2.32 | |
| BS-PP-12 | 0.42 | 2.14 | 0.86 |
| BS-PP-15 | 0.76 | 2 | |

| Compounds | NB4 | |
| --- | --- | --- |
| | $IC_{50}$ | $IC_{90}$ |
| PP | 1.84 | 6.75 |
| BS-PP-03 | 1.13 | 1.96 |
| BS-PP-04 | 0.91 | 3.85 |
| BS-PP-06 | 0.79 | 4.09 |
| BS-PP-07 | 1.09 | |
| BS-PP-08 | 0.85 | 1.90 |
| BS-PP-09 | 1.11 | 3.92 |
| BS-PP-10 | 0.83 | 2.82 |
| BS-PP-11 | 0.94 | 2.48 |
| BS-PP-12 | 1.22 | 3.96 |
| BS-PP-15 | 1.19 | 3.40 |

Example 3

Evaluation of the Anti-Human Solid Tumor Effects by the Polyphyllin I Derivatives with 5'-Acylated Arabinofuranosyl Groups of the Present Invention (1) Experimental Materials Human solid tumor cell lines: A549 (human lung cancer) and SK-OV-3 (ovarian cancer cell), all of which are purchased from China Center For Type Culture Collection; RKO (human colon adenocarcinoma cell) and MG-63 (osteosarcoma), all of which are purchased from Fuxiang Bio-tech Co. Ltd., Shanghai, China; Hela (human cervical cancer cell), donated by Cancer Research Institute of Zhejiang University, China.

Reagents: the same as in Example 2.

Main apparatuses: a Thermo Scientific 3111 incubator and a Bio-Rad iMark microplate reader.

(2) Experimental Method 4000 well-growing human solid tumor cells were obtained and inoculated into wells of a 96-well cell culture plate. The culture medium used was DMEM High Glucose cell culture medium containing 10% fetal bovine serum. The plate is placed in a carbon dioxide cell incubator (5% $CO_2$) at 37° C. and incubated for 24 hours. After adding the Polyphyllin I derivatives with 5'-acylated arabinofuranosyl group of different concentrations and mixing uniformly, the plate was continued to be placed in a carbon dioxide cell incubator (5% $CO_2$) at 37° C. and incubated for 72 hours. Then the viable cell concentration was determined by the MTT method and the cell viability (%) after drug treatment was calculated. In this experiment, the cell viability of control group (not treated with any compound) is set as 100%.

(3) Experimental Results

The experimental results are shown in Table 2. Table 2 shows that the Polyphyllin I derivatives with 5'-acylated arabinofuranosyl group of the present invention can induce the death of human solid tumor cells and inhibit the growth of these tumor cells. Compared with Polyphyllin I itself, the Polyphyllin I derivatives with 5'-acylated arabinofuranosyl group of the present invention exhibit significantly enhanced anti-human solid tumor cell activities. Specifically, the Polyphyllin I derivatives of the present invention BS-PP-04, BS-PP-08, BS-PP-10, BS-PP-11, and BS-PP-12 exhibit particularly significant activities and improve the anti-A549 (human lung cancer) activity by more than 2-fold.

TABLE 2

Determination of the half inhibiting concentrations of the Polyphyllin I derivatives with 5'-acylated arabinofuranosyl on the growth of human myeloma cells and human solid tumor cells (72 h, $IC_{50}$ (µg/mL) value and $IC_{90}$ (µg/mL) value).

| Compounds | A549 | |
| --- | --- | --- |
| | $IC_{50}$ | $IC_{90}$ |
| PP I | 1.86 | 14.63 |
| BS-PP-04 | 1 | 14.47 |
| BS-PP-05 | 1.8 | 12 |
| BS-PP-08 | 1.19 | 14.08 |
| BS-PP-09 | 1.6 | 13 |
| BS-PP-10 | 0.86 | 10.23 |
| BS-PP-11 | 0.83 | 10.19 |
| BS-PP-12 | 0.86 | 7.38 |
| BS-PP-15 | 1.8 | 9.9 |

| Compounds | RKO |
| --- | --- |
| | $IC_{90}$ |
| PP I | 8.48 |
| BS-PP-03 | 4.50 |
| BS-PP-05 | 6.82 |
| BS-PP-06 | 5.13 |
| BS-PP-08 | 4.93 |
| BS-PP-09 | 5.25 |
| BS-PP-10 | 5.46 |
| BS-PP-12 | 6.08 |
| BS-PP-15 | 5.13 |

| Compounds | MG-63 | | Hela | |
| --- | --- | --- | --- | --- |
| | $IC_{50}$ | $IC_{90}$ | $IC_{50}$ | $IC_{90}$ |
| PP | 0.37 | 0.97 | 0.77 | 4.86 |
| BS-PP-04 | | | 0.48 | 3.23 |
| BS-PP-08 | | | 0.61 | 3.89 |
| BS-PP-09 | | | 0.55 | 2.00 |
| BS-PP-10 | 0.33 | 0.85 | 0.45 | 2.01 |
| BS-PP-11 | 0.33 | 0.76 | 0.62 | 2.57 |
| BS-PP-12 | | | 0.50 | 3.19 |
| BS-PP-15 | | | 0.68 | 3.51 |

TABLE 2-continued

Determination of the half inhibiting concentrations of the Polyphyllin I derivatives with 5'-acylated arabinofuranosyl on the growth of human myeloma cells and human solid tumor cells (72 h, $IC_{50}$ (μg/mL) value and $IC_{90}$ (μg/mL) value).

| Compounds | SK-OV-3 | |
| --- | --- | --- |
| | $IC_{50}$ | $IC_{90}$ |
| PP | 0.70 | 1.70 |
| BS-PP-10 | 0.65 | 0.97 |

The invention claimed is:

1. A Polyphyllin I derivative with 5'-acylated arabinofuranosyl group, as shown in formula I:

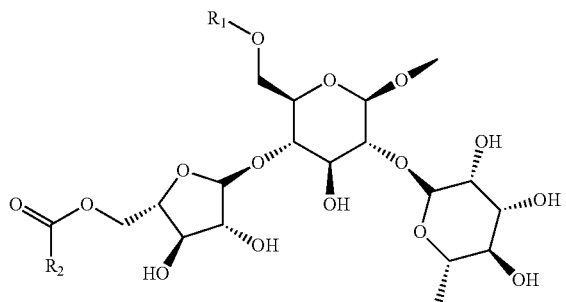

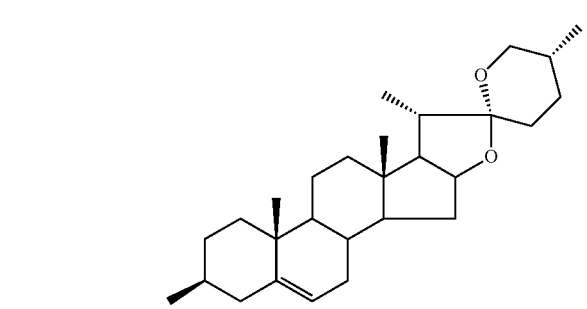

wherein
$R_1$ is selected from H, substituted or unsubstituted $C_1$-$C_6$ alkyl, substituted or unsubstituted $C_2$-$C_6$ alkenyl, substituted or unsubstituted $C_3$-$C_7$ cycloalkyl, substituted or unsubstituted $C_3$-$C_7$ cycloalkenyl, substituted or unsubstituted aryl $C_1$-$C_6$ alkyl, substituted or unsubstituted heterocyclyl, substituted or unsubstituted heteroaryl, substituted or unsubstituted $C_1$-$C_6$ alkylacyl or substituted or unsubstituted arylacyl;

$R_2$ is selected from H, substituted or unsubstituted $C_1$-$C_6$ alkyl, substituted or unsubstituted $C_2$-$C_6$ alkenyl, substituted or unsubstituted $C_3$-$C_7$ cycloalkyl, substituted or unsubstituted $C_3$-$C_7$ cycloalkenyl, substituted or unsubstituted aryl, substituted or unsubstituted heterocyclyl, or substituted or unsubstituted heteroaryl;

the substituent in the aforementioned substituted groups is one or more selected from halogen, amino, —$NH_{2-n}$($C_1$-$C_6$ alkyl)$_n$, —$NH_{2-n}$($C_3$-$C_7$ cycloalkyl)$_n$, nitro, cyano, hydroxyl, trifluoromethyl, $C_1$-$C_6$ alkoxy, thiol or $C_1$-$C_6$ alkylthio; wherein n is an integer selected from 1 or 2;

or a pharmaceutically acceptable adduct, complex or salt thereof.

2. The Polyphyllin I derivative with 5'-acylated arabinofuranosyl or the pharmaceutically acceptable salt thereof according to claim 1, wherein $R_1$ is H.

3. The Polyphyllin I derivative with 5'-acylated arabinofuranosyl or the pharmaceutically acceptable salt thereof according to claim 1, wherein $R_2$ is substituted or unsubstituted aryl, said aryl being phenyl.

4. The Polyphyllin I derivative with 5'-acylated arabinofuranosyl or the pharmaceutically acceptable salt thereof according to claim 1, wherein $R_2$ is substituted or unsubstituted heteroaryl, said heteroaryl being a five-membered or six-membered aromatic ring radical containing nitrogen, oxygen or sulfur heteroatoms.

5. The Polyphyllin I derivative with 5'-acylated arabinofuranosyl or the pharmaceutically acceptable salt thereof according to claim 4, wherein the heteroaryl is furanyl, thienyl, or pyridyl.

6. The Polyphyllin I derivative with 5'-acylated arabinofuranosyl or the pharmaceutically acceptable salt thereof according to claim 1, wherein $R_2$ is substituted or unsubstituted $C_1$-$C_6$ alkyl, substituted or unsubstituted $C_2$-$C_6$ alkenyl, substituted or unsubstituted $C_3$-$C_7$ cycloalkyl, substituted or unsubstituted $C_3$-$C_7$ cycloalkenyl.

7. The Polyphyllin I derivative with 5'-acylated arabinofuranosyl or the pharmaceutically acceptable salt thereof according to claim 6, wherein $R_2$ is cyclopropyl or methyl.

8. The Polyphyllin I derivative with 5'-acylated arabinofuranosyl or the pharmaceutically acceptable salt thereof according to claim 3, wherein $R_2$ is substituted with one or more substituents selected from halogen, amino, —$NH_{2-n}$ ($C_1$-$C_6$ alkyl)$_n$, —$NH_{2-n}$($C_3$-$C_7$ cycloalkyl)$_n$, nitro, cyano, hydroxyl, trifluoromethyl, $C_1$-$C_6$ alkoxy, thiol or $C_1$-$C_6$ alkylthio, wherein n is an integer selected from 1 or 2

9. The Polyphyllin I derivative with 5'-acylated arabinofuranosyl or the pharmaceutically acceptable salt thereof according to claim 8, wherein the substituent is fluoro, chloro, methoxyl, trifluoromethyl, or dimethylamino.

10. The Polyphyllin I derivative with 5'-acylated arabinofuranosyl or the pharmaceutically acceptable salt thereof according to claim 1, which is a compound selected from the group consisting of

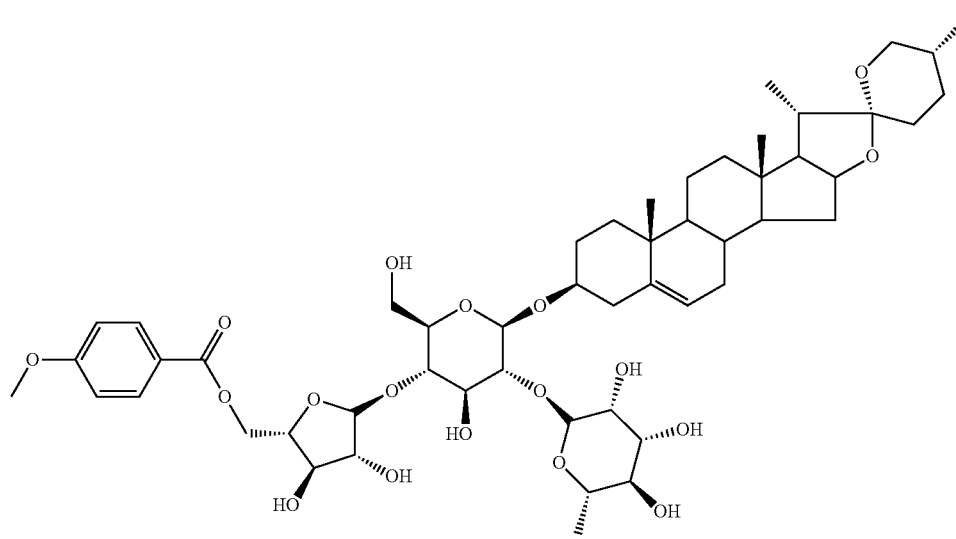
4-O-(5'-O-(4-methoxybenzoyl)arabinofuranosyl-2-O-rhamnopyranosyl-β-D-glucopyranosyldioscin
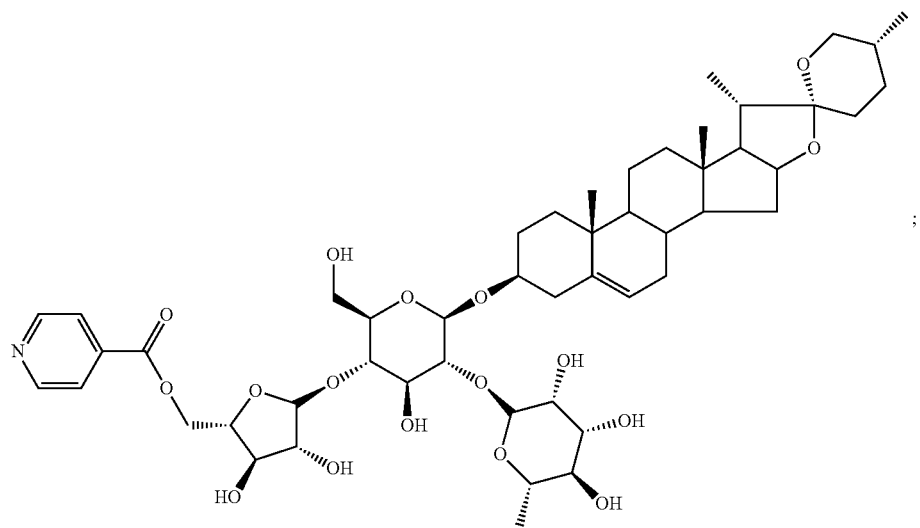
4-O-(5'-O-(4-pyridinylformyl) arabinofuranosyl-2-O-rhamnopyranosyl-β-D-glucopyyranosyldioscin

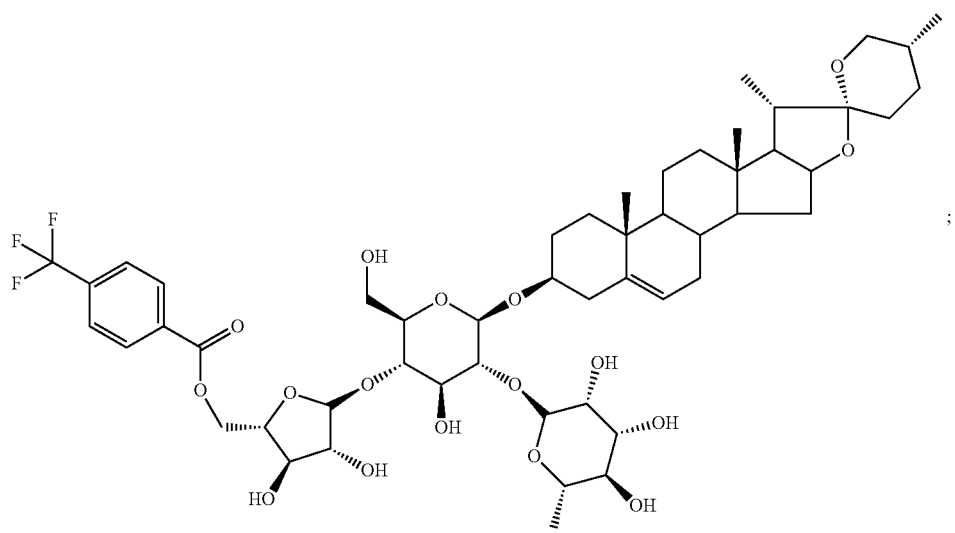
4-O-(5'-O-(4-trifluoromethylbenzoyl)
arabinofuranosyl-2-O-rhamnopyranosyl-β-D-glucopyranosyldioscin
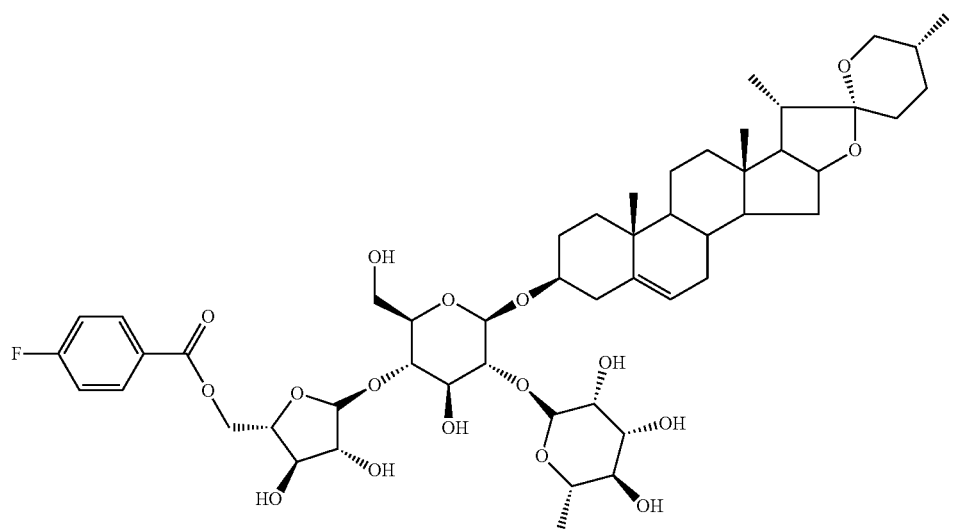
4-O-(5'-O-(4-fluorobenzoyl) arabinofuranosyl-2-O-rhamnopyranosyl-β-D-glucopyranosyldioscin -continued
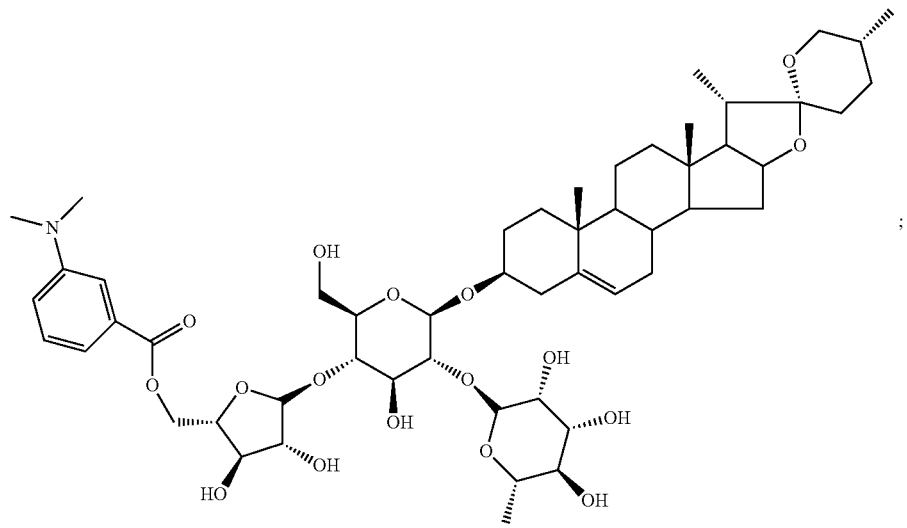
4-O-(5′-O-(4-dimethylaminobenzoyl) arabinofuranosyl-2-O-rhamnopyranosyl-β-D-glucopyranosyldioscin
BS-PP-07
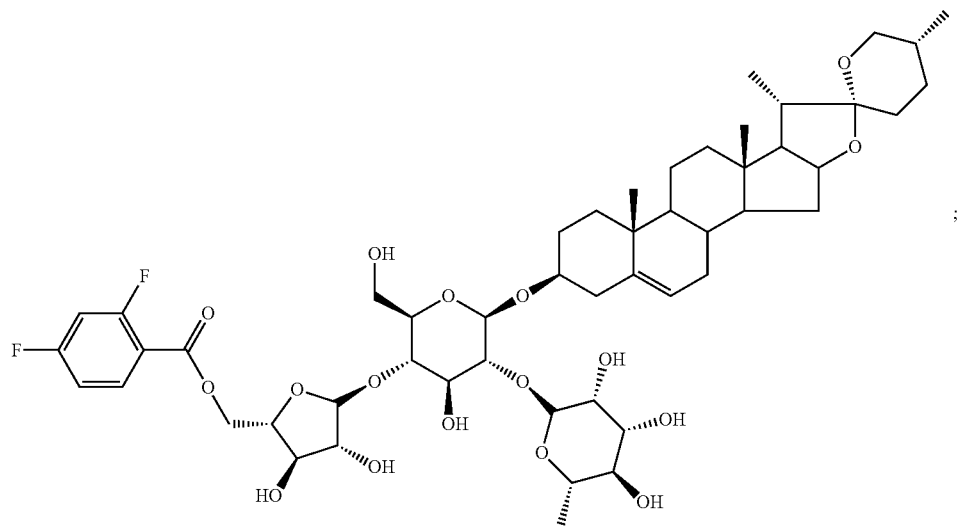
4-O-(5′-O-(2,4-difluorobenzoyl) arabinofuranosyyl-2-O-rhamnopyranosyl-β-D-glucopyranosyldioscin
BS-PP-08

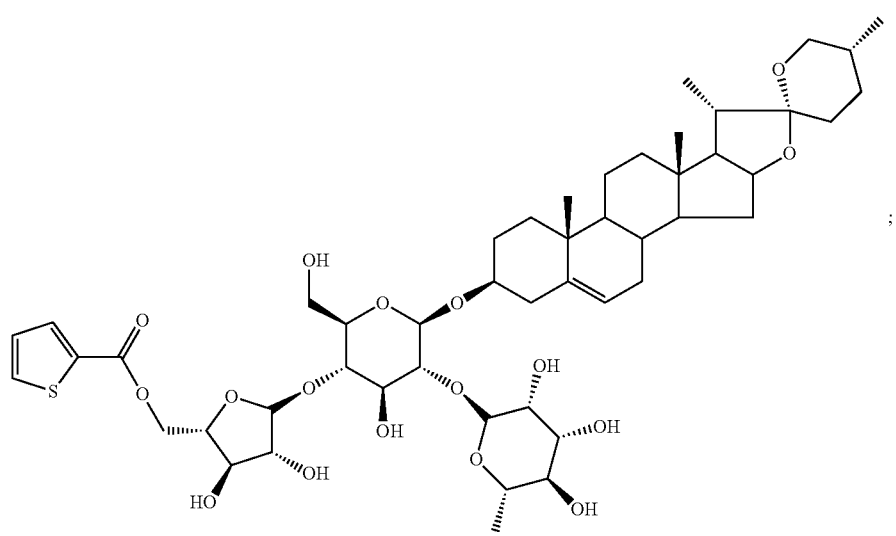
4-O-(5'-O-(2-thiopheneformyl) arabinofuranosyl-2-O-rhamnopyranosyl-β-D-glucoyranosyldioscin
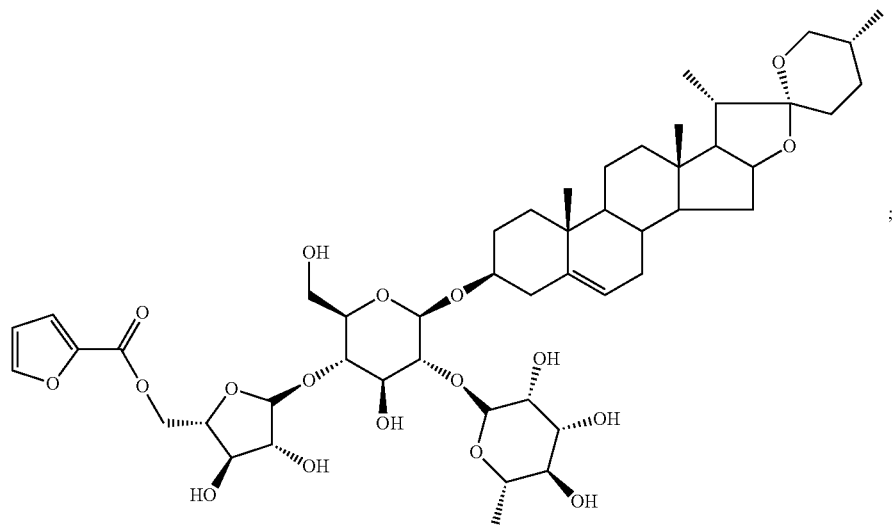
4-O-(5'-O-(2-furanylformyl) arabinofuranosyl-2-O-rhamnoyranosyl-β-D-glucopyranosyldioscin

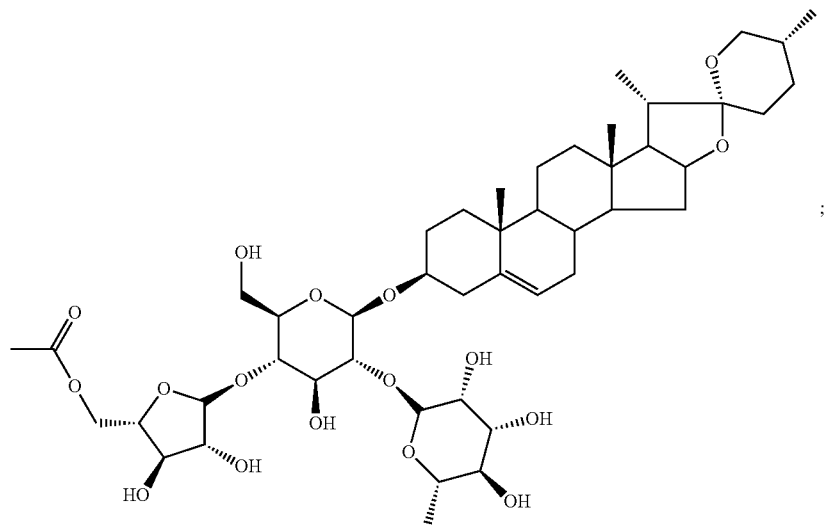
4-O-(5′-O-acetyl) arabinofuranosyl-2-O-rhamnopyranosyl-β-D-glucopyranosyldioscin
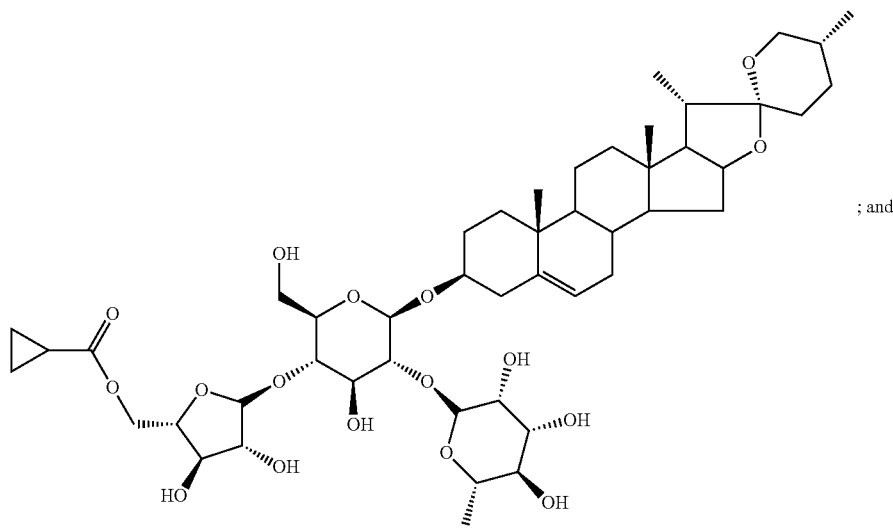
4-O-(5′-O-cyclopropylformyl) arabinofuranosyl-2-O-rhamnoyranosyl-β-D-glucopyranosyldioscin

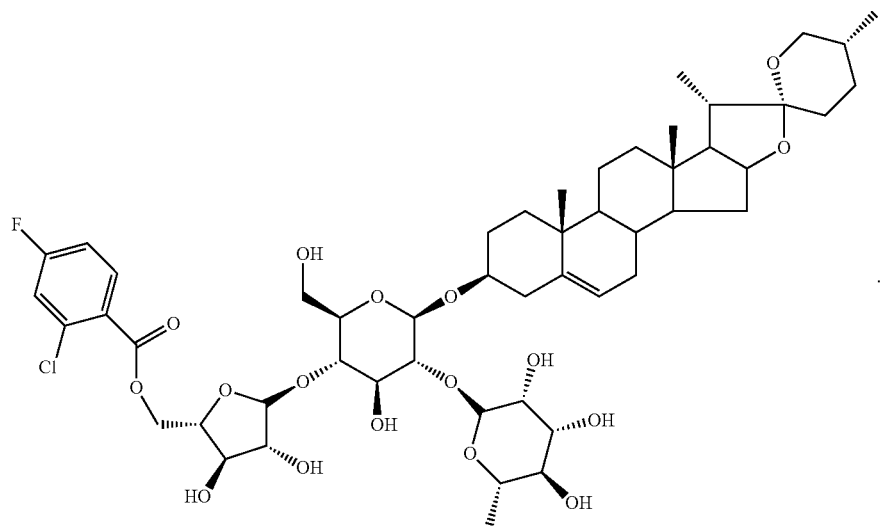

4-O-(5'-O-(2-chloro-4-fluorobenzoyl)
arabinofuranosyl-2-O-rhamnopyranosyl-β-D-glucopyranosyldioscin

BS-PP-15

11. A process for preparing the compound of formula (I) according to claim 1,
comprising the condensation esterification of Polyphyllin I

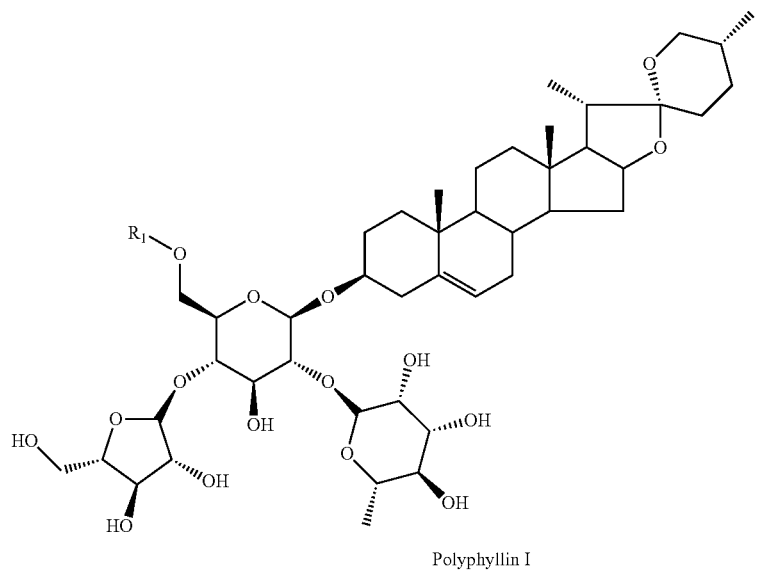

Polyphyllin I and the corresponding organic acid $R_2CO_2H$ in the presence of a condensation agent or a catalyst, or comprising the condensation esterification of Polyphyllin I and the corresponding organic acyl chloride $R_2COCl$ or organic anhydride $(R_2CO)_2O$ in the presence of a condensation agent or an alkaline reagent to produce a Polyphyllin I derivative

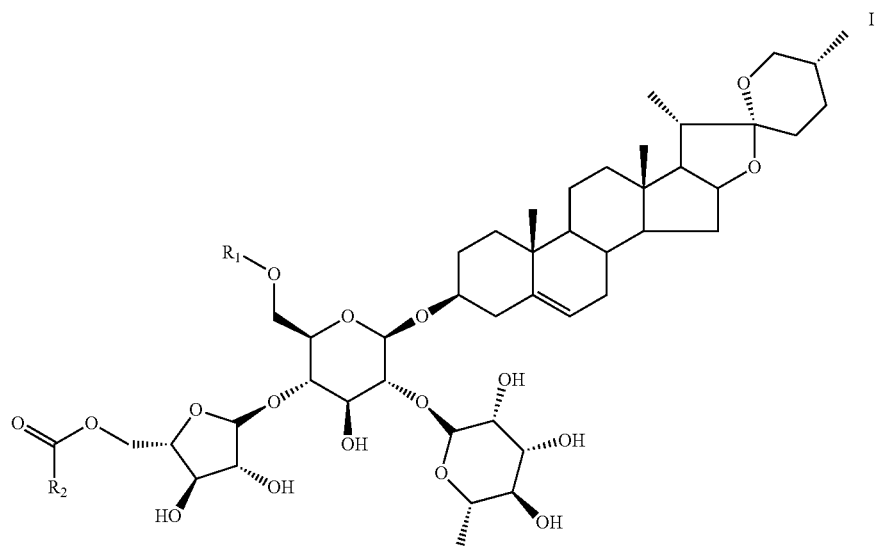

with 5'-acylated arabinofuranosyl, wherein $R_2$ and $R_1$ in formula (I), $R_2$ in the organic acid $R_2CO_2H$, and $R_2$ in the organic acyl chloride $R_2COCl$ are defined according to claim 1.

12. A pharmaceutical composition, comprising the Polyphyllin I derivative with 5'-acylated arabinofuranosyl or a pharmaceutically acceptable salt thereof according to claim 1 and optionally a pharmaceutically acceptable excipient.

13. A method for treating a tumor in a subject, comprising administrating to the subject in need thereof an effective amount of the Polyphyllin I derivative with 5'-acylated arabinofuranosyl or a pharmaceutically acceptable salt thereof according to claim 1, wherein said treating refers to inhibiting or relieving the symptoms of the tumor in the subject.

14. The Polyphyllin I derivative with 5'-acylated arabinofuranosyl or a pharmaceutically acceptable salt thereof according to claim 1 for use as an antitumor agent.

15. The method of claim 13, wherein the tumor is selected from the group consisting of leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma and prostate cancer.

* * * * *